United States Patent
Cowan et al.

(10) Patent No.: US 11,752,005 B2
(45) Date of Patent: Sep. 12, 2023

(54) EXPANDABLE SPINAL IMPLANT SYSTEM AND METHOD OF USING SAME

(71) Applicant: Warsaw Orthopedic, Inc., Warsaw, IN (US)

(72) Inventors: Benjamin D. Cowan, Memphis, TN (US); Cristian A. Capote, Memphis, TN (US); Keith E. Miller, Germantown, TN (US); Zain Noordin, Collierville, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 81 days.

(21) Appl. No.: 17/086,625

(22) Filed: Nov. 2, 2020

(65) Prior Publication Data

US 2021/0068974 A1    Mar. 11, 2021

Related U.S. Application Data

(62) Division of application No. 16/282,661, filed on Feb. 22, 2019, now Pat. No. 10,856,997.
(Continued)

(51) Int. Cl.
*A61F 2/44*    (2006.01)
*A61F 2/46*    (2006.01)
*A61F 2/30*    (2006.01)

(52) U.S. Cl.
CPC .......... *A61F 2/4425* (2013.01); *A61F 2/447* (2013.01); *A61F 2/30771* (2013.01);
(Continued)

(58) Field of Classification Search
CPC .. A61F 2002/30556; A61F 2002/30545; A61F 2002/30281; A61F 2002/30266; A61F 2002/30553
See application file for complete search history.

(56) References Cited

U.S. PATENT DOCUMENTS

| | | |
|---|---|---|
| 4,401,112 A | 8/1983 | Rezaian |
| 4,553,273 A | 11/1985 | Wu |

(Continued)

FOREIGN PATENT DOCUMENTS

| | | |
|---|---|---|
| DE | 44 16 605 C1 | 6/1995 |
| EP | 0 767 636 A1 | 4/1997 |

(Continued)

OTHER PUBLICATIONS

International Search Report, and Written Opinion for Application. No. PCT/US2019/019067, dated Jun. 3, 2019.
(Continued)

*Primary Examiner* — Jan Christopher L Merene
(74) *Attorney, Agent, or Firm* — FOX ROTHSCHILD LLP; P. Marshall Ticer

(57) ABSTRACT

An expandable spinal implant is provided having first and second endplates hinged along one end or otherwise connected by pins, protrusions and channels, or similar mechanisms and an expansion mechanism(s) disposed therebetween configured to expand the first and second endplates from each other. Also provided are expandable spinal implants that may be expanded in a parallel manner to increase the height of the device while maintaining a lordotic angle. Other spinal implants may provide dual expansion whereby both height and lordotic angle are adjusted. Various implants, systems and methods are disclosed.

17 Claims, 31 Drawing Sheets

Related U.S. Application Data

(60) Provisional application No. 62/652,742, filed on Apr. 4, 2018, provisional application No. 62/634,033, filed on Feb. 22, 2018.

(52) U.S. Cl.
CPC ... *A61F 2/4611* (2013.01); *A61F 2002/30471* (2013.01); *A61F 2002/30556* (2013.01); *A61F 2002/30579* (2013.01); *A61F 2002/4629* (2013.01); *A61F 2220/0025* (2013.01); *A61F 2310/00023* (2013.01)

(56) References Cited

U.S. PATENT DOCUMENTS

| | | |
|---|---|---|
| 4,636,217 A | 1/1987 | Ogilvie et al. |
| 4,759,769 A | 7/1988 | Hedman et al. |
| 5,059,193 A | 10/1991 | Kuslich |
| 5,171,278 A | 12/1992 | Pisharodi |
| 5,336,223 A | 8/1994 | Rogers |
| 5,390,683 A | 2/1995 | Pisharodi |
| 5,522,899 A | 6/1996 | Michelson |
| 5,554,191 A | 9/1996 | Lahille et al. |
| 5,575,790 A | 11/1996 | Chen et al. |
| 5,609,635 A | 3/1997 | Michelson |
| 5,653,762 A | 8/1997 | Pisharodi |
| 5,658,336 A | 8/1997 | Pisharodi |
| 5,665,122 A | 9/1997 | Kambin |
| 5,693,100 A | 12/1997 | Pisharodi |
| 5,697,977 A | 12/1997 | Pisharodi |
| 5,702,391 A | 12/1997 | Lin |
| 5,702,453 A | 12/1997 | Rabbe et al. |
| 5,702,455 A | 12/1997 | Saggar |
| 5,800,550 A | 9/1998 | Sertich |
| 5,865,848 A | 2/1999 | Baker |
| 5,893,890 A | 4/1999 | Pisharodi |
| 5,980,522 A | 11/1999 | Koros et al. |
| 6,045,579 A | 4/2000 | Hochshuler et al. |
| 6,080,193 A | 6/2000 | Hochshuler et al. |
| 6,099,531 A | 8/2000 | Bonutti |
| 6,102,949 A | 8/2000 | Biedermann et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,132,465 A | 10/2000 | Ray et al. |
| 6,159,211 A | 12/2000 | Boriani et al. |
| 6,159,244 A | 12/2000 | Suddaby |
| 6,176,882 B1 | 1/2001 | Biedermann et al. |
| 6,179,873 B1 | 1/2001 | Zientek |
| 6,190,414 B1 | 2/2001 | Young et al. |
| 6,193,757 B1 | 2/2001 | Foley et al. |
| 6,217,579 B1 | 4/2001 | Koros |
| 6,245,108 B1 | 6/2001 | Biscup |
| 6,309,421 B1 | 10/2001 | Pisharodi |
| 6,342,074 B1 | 1/2002 | Simpson |
| 6,371,989 B1 | 4/2002 | Chauvin et al. |
| 6,395,031 B1 | 5/2002 | Foley et al. |
| 6,423,063 B1 | 7/2002 | Bonutti |
| 6,432,106 B1 | 8/2002 | Fraser |
| 6,436,140 B1 | 8/2002 | Liu et al. |
| 6,443,989 B1 | 9/2002 | Jackson |
| 6,443,990 B1 | 9/2002 | Aebi et al. |
| 6,454,806 B1 | 9/2002 | Cohen et al. |
| 6,454,807 B1 | 9/2002 | Jackson |
| 6,461,359 B1 | 10/2002 | Tribus et al. |
| 6,491,724 B1 | 12/2002 | Ferree |
| 6,520,991 B2 | 2/2003 | Huene |
| 6,520,993 B2 | 2/2003 | James et al. |
| 6,527,803 B1 | 3/2003 | Crozet et al. |
| 6,562,074 B2 | 5/2003 | Gerbec et al. |
| 6,576,016 B1 | 6/2003 | Hochshuler et al. |
| 6,623,525 B2 | 9/2003 | Ralph et al. |
| 6,629,998 B1 | 10/2003 | Lin |
| 6,635,086 B2 | 10/2003 | Lin |
| 6,648,917 B2 | 11/2003 | Gerbec et al. |
| 6,676,703 B2 | 1/2004 | Biscup |
| 6,770,096 B2 | 8/2004 | Bolger et al. |
| 6,773,460 B2 | 8/2004 | Jackson |
| 6,821,298 B1 | 11/2004 | Jackson |
| 6,835,206 B2 | 12/2004 | Jackson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,923,814 B1 | 8/2005 | Hildebrand et al. |
| 6,926,737 B2 | 8/2005 | Jackson |
| 6,964,687 B1 | 11/2005 | Bernard et al. |
| 6,974,480 B2 | 12/2005 | Messerli et al. |
| 6,984,234 B2 | 1/2006 | Bray |
| 7,112,222 B2 | 9/2006 | Fraser et al. |
| 7,135,043 B2 | 11/2006 | Nakahara et al. |
| 7,137,997 B2 | 11/2006 | Paul |
| 7,172,627 B2 | 2/2007 | Fiere et al. |
| 7,204,853 B2 | 4/2007 | Gordon et al. |
| 7,232,464 B2 | 6/2007 | Mathieu et al. |
| 7,238,203 B2 | 7/2007 | Bagga et al. |
| 7,316,714 B2 | 1/2008 | Gordon et al. |
| 7,618,456 B2 | 11/2009 | Mathieu et al. |
| 7,708,778 B2 | 5/2010 | Gordon et al. |
| 7,727,280 B2 | 6/2010 | McLuen |
| 7,753,958 B2 | 7/2010 | Gordon et al. |
| 7,806,932 B2 | 10/2010 | Webb et al. |
| 7,815,682 B1 | 10/2010 | Peterson et al. |
| 7,846,207 B2 | 12/2010 | Lechmann et al. |
| 7,850,731 B2 | 12/2010 | Brittan et al. |
| 7,850,733 B2 | 12/2010 | Baynham et al. |
| 7,862,616 B2 | 1/2011 | Lechmann et al. |
| 7,875,076 B2 | 1/2011 | Mathieu et al. |
| 7,909,869 B2 | 3/2011 | Gordon et al. |
| 8,118,870 B2 | 2/2012 | Gordon et al. |
| 8,118,871 B2 | 2/2012 | Gordon et al. |
| 8,182,539 B2 | 5/2012 | Tyber et al. |
| 8,287,597 B1 | 10/2012 | Pimenta et al. |
| 8,425,528 B2 | 4/2013 | Berry et al. |
| 8,641,768 B2 | 2/2014 | Duffield et al. |
| 8,647,386 B2 | 2/2014 | Gordon et al. |
| 8,685,098 B2 | 4/2014 | Glerum et al. |
| 8,709,083 B2 | 4/2014 | Duffield et al. |
| 8,709,085 B2 | 4/2014 | Lechmann et al. |
| 8,715,353 B2 | 5/2014 | Bagga et al. |
| 8,795,366 B2 | 8/2014 | Varela |
| 8,808,305 B2 | 8/2014 | Kleiner |
| 8,852,282 B2 | 10/2014 | Farley et al. |
| 8,894,708 B2 | 11/2014 | Thalgott et al. |
| 8,906,095 B2 | 12/2014 | Christensen et al. |
| 8,920,500 B1 | 12/2014 | Pimenta et al. |
| 8,926,704 B2 | 1/2015 | Glerum et al. |
| 9,005,293 B2 | 4/2015 | Moskowitz et al. |
| 9,005,295 B2 | 4/2015 | Kueenzi et al. |
| 9,034,045 B2 | 5/2015 | Davenport et al. |
| 9,060,877 B2 | 6/2015 | Kleiner |
| 9,125,757 B2 | 9/2015 | Weiman |
| 9,132,021 B2 | 9/2015 | Mermuys et al. |
| 9,138,330 B2 | 9/2015 | Hansell et al. |
| 9,149,367 B2 | 10/2015 | Davenport et al. |
| 9,155,631 B2 | 10/2015 | Seifert et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,198,772 B2 | 12/2015 | Weiman |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,351,845 B1 | 5/2016 | Pimenta et al. |
| 9,351,848 B2 | 5/2016 | Glerum et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,343 B2 | 6/2016 | Duffield et al. |

(56) References Cited

U.S. PATENT DOCUMENTS

| | | | |
|---|---|---|---|
| 9,370,434 B2 | 6/2016 | Weiman | |
| 9,370,435 B2 | 6/2016 | Walkenhorst et al. | |
| 9,387,092 B2 | 7/2016 | Mermuys et al. | |
| 9,414,937 B2 | 8/2016 | Carlson et al. | |
| 9,452,063 B2 | 9/2016 | Glerum et al. | |
| 9,456,906 B2 | 10/2016 | Gray et al. | |
| 9,474,625 B2 | 10/2016 | Weiman | |
| 9,480,573 B2 | 11/2016 | Perloff et al. | |
| 9,480,576 B2 | 11/2016 | Pepper et al. | |
| 9,480,579 B2 | 11/2016 | Davenport et al. | |
| 9,486,325 B2 | 11/2016 | Davenport et al. | |
| 9,492,287 B2 | 11/2016 | Glerum et al. | |
| 9,492,288 B2 | 11/2016 | Wagner et al. | |
| 9,492,289 B2 | 11/2016 | Davenport et al. | |
| 9,510,954 B2 | 12/2016 | Glerum et al. | |
| 9,532,821 B2 | 1/2017 | Moskowitz et al. | |
| 9,561,116 B2 | 2/2017 | Weiman et al. | |
| 9,566,168 B2 | 2/2017 | Glerum et al. | |
| 9,572,677 B2 | 2/2017 | Davenport et al. | |
| 9,579,124 B2 | 2/2017 | Gordon et al. | |
| 9,585,762 B2 | 3/2017 | Suddaby et al. | |
| 9,603,713 B2 | 3/2017 | Moskowitz et al. | |
| 9,622,875 B2 | 4/2017 | Moskowitz et al. | |
| 9,629,729 B2 | 4/2017 | Grimberg, Jr. et al. | |
| 9,655,746 B2 | 5/2017 | Seifert | |
| 9,655,747 B2 | 5/2017 | Glerum et al. | |
| 9,662,224 B2 | 5/2017 | Weiman et al. | |
| 9,675,467 B2 | 6/2017 | Duffield et al. | |
| 9,700,428 B2 | 7/2017 | Niemiec et al. | |
| 9,707,092 B2 | 7/2017 | Davenport et al. | |
| 9,713,536 B2 | 7/2017 | Foley et al. | |
| 9,717,601 B2 * | 8/2017 | Miller | A61F 2/4611 |
| 9,730,684 B2 | 8/2017 | Beale et al. | |
| 9,801,733 B2 | 10/2017 | Wolters et al. | |
| 10,299,934 B2 * | 5/2019 | Seifert | A61F 2/4455 |
| 10,842,642 B2 * | 11/2020 | Pimenta | A61B 17/8685 |
| 2002/0045943 A1 | 4/2002 | Uk | |
| 2002/0045945 A1 | 4/2002 | Liu et al. | |
| 2002/0116066 A1 | 8/2002 | Chauvin et al. | |
| 2002/0128713 A1 | 9/2002 | Ferree | |
| 2002/0151976 A1 | 10/2002 | Foley et al. | |
| 2003/0050701 A1 | 3/2003 | Michelson | |
| 2003/0130739 A1 | 7/2003 | Gerbec et al. | |
| 2004/0172134 A1 | 9/2004 | Berry | |
| 2004/0186570 A1 | 9/2004 | Rapp | |
| 2004/0193158 A1 | 9/2004 | Lim et al. | |
| 2004/0249461 A1 | 12/2004 | Ferree | |
| 2004/0254643 A1 | 12/2004 | Jackson | |
| 2004/0254644 A1 | 12/2004 | Taylor | |
| 2005/0015149 A1 | 1/2005 | Michelson | |
| 2005/0033429 A1 | 2/2005 | Kuo | |
| 2005/0033439 A1 | 2/2005 | Gordon et al. | |
| 2006/0058880 A1 * | 3/2006 | Wysocki | A61F 2/4425 606/90 |
| 2008/0140207 A1 * | 6/2008 | Olmos | A24F 47/00 623/17.11 |
| 2010/0125334 A1 * | 5/2010 | Krueger | A61F 2/442 606/86 R |
| 2011/0144755 A1 * | 6/2011 | Baynham | A61F 2/447 623/17.16 |
| 2013/0204371 A1 * | 8/2013 | McLuen | A61F 2/4465 623/17.16 |
| 2013/0211526 A1 * | 8/2013 | Alheidt | A61F 2/442 623/17.16 |
| 2014/0114420 A1 | 4/2014 | Robinson | |
| 2014/0236296 A1 * | 8/2014 | Wagner | A61F 2/4455 623/17.15 |
| 2014/0243982 A1 | 8/2014 | Miller | |
| 2014/0277500 A1 | 9/2014 | Logan et al. | |
| 2015/0223946 A1 * | 8/2015 | Weiman | A61F 2/442 623/17.15 |
| 2016/0008924 A1 | 1/2016 | Canourgues et al. | |
| 2016/0089247 A1 | 3/2016 | Nichols et al. | |
| 2017/0010025 A1 | 1/2017 | Mayershofer | |
| 2017/0029635 A1 | 2/2017 | Doll et al. | |
| 2017/0049651 A1 | 2/2017 | Lim et al. | |
| 2017/0049653 A1 | 2/2017 | Lim et al. | |
| 2017/0095345 A1 | 4/2017 | Davenport et al. | |
| 2017/0100255 A1 | 4/2017 | Hleihil et al. | |
| 2017/0105844 A1 | 4/2017 | Kuyler et al. | |
| 2017/0224504 A1 | 8/2017 | Butler et al. | |
| 2017/0296352 A1 | 10/2017 | Richerme et al. | |
| 2018/0030362 A1 | 2/2018 | Kosler et al. | |
| 2018/0031810 A1 | 2/2018 | Hsu et al. | |
| 2018/0036138 A1 | 2/2018 | Robinson | |
| 2018/0078380 A1 * | 3/2018 | Stampfli | A61F 2/447 |
| 2018/0116891 A1 | 5/2018 | Beale et al. | |
| 2018/0193160 A1 * | 7/2018 | Hsu | A61F 2/447 |
| 2018/0303621 A1 | 10/2018 | Brotman et al. | |
| 2018/0318101 A1 * | 11/2018 | Engstrom | A61F 2/442 |
| 2019/0000702 A1 | 1/2019 | Lim et al. | |
| 2019/0000707 A1 | 1/2019 | Lim et al. | |
| 2019/0020121 A1 | 1/2019 | Paulotto et al. | |
| 2019/0046381 A1 | 2/2019 | Lim et al. | |
| 2019/0046383 A1 | 2/2019 | Lim et al. | |
| 2019/0201210 A1 | 7/2019 | Besaw et al. | |

FOREIGN PATENT DOCUMENTS

| | | |
|---|---|---|
| EP | 0 880 950 A1 | 12/1998 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| GB | 2 377 387 A | 1/2003 |
| WO | 92/14423 A1 | 9/1992 |
| WO | 97/ 00054 A1 | 1/1997 |
| WO | 99/ 26562 A1 | 6/1999 |
| WO | 99/66867 A1 | 12/1999 |
| WO | 00/12033 A1 | 3/2000 |
| WO | 00/25706 A1 | 5/2000 |
| WO | 00/ 49977 A1 | 8/2000 |
| WO | 02/19952 A1 | 3/2002 |
| WO | 03/105673 A2 | 12/2003 |
| WO | 2014/133755 A1 | 9/2014 |
| WO | 2017/168208 A1 | 10/2017 |

OTHER PUBLICATIONS

International Search Report and Written Opinion for Application No. PCT/US2019/019060, dated Jun. 5, 2019.

Supplementary European Search Report issued in EP 19757816.4 dated Nov. 17, 2021.

Chinese Office Action in Application No. 201980012670.6 dated Mar. 1, 2023.

* cited by examiner

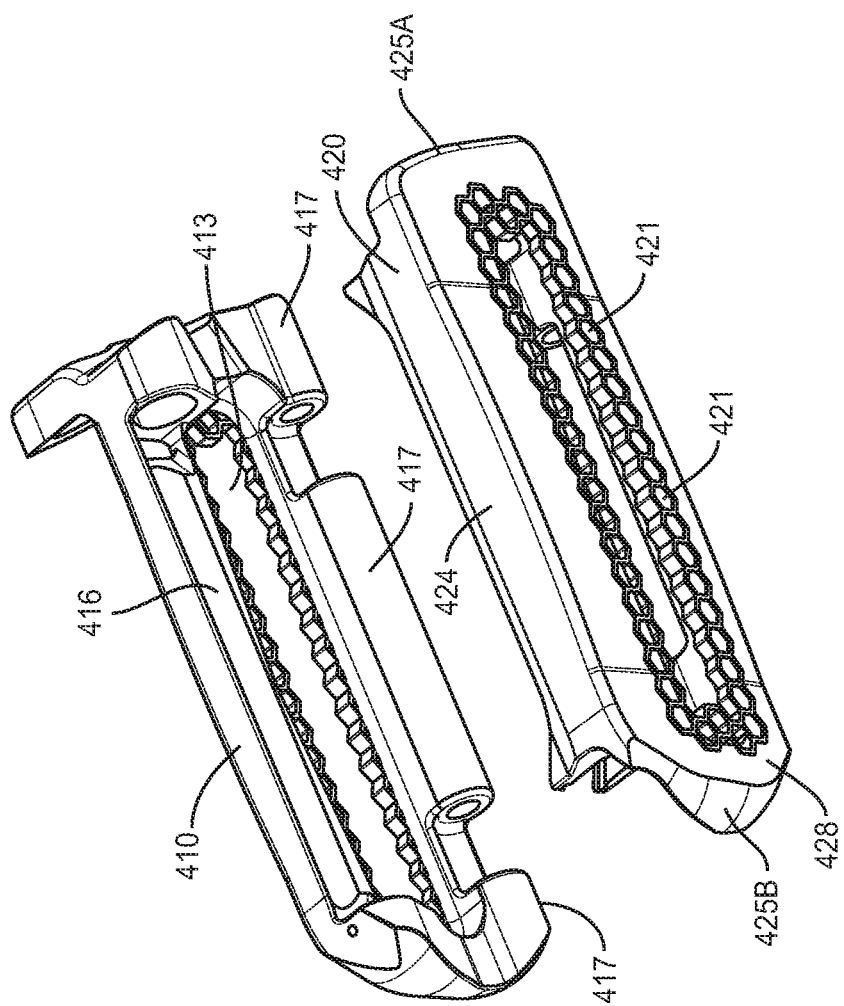
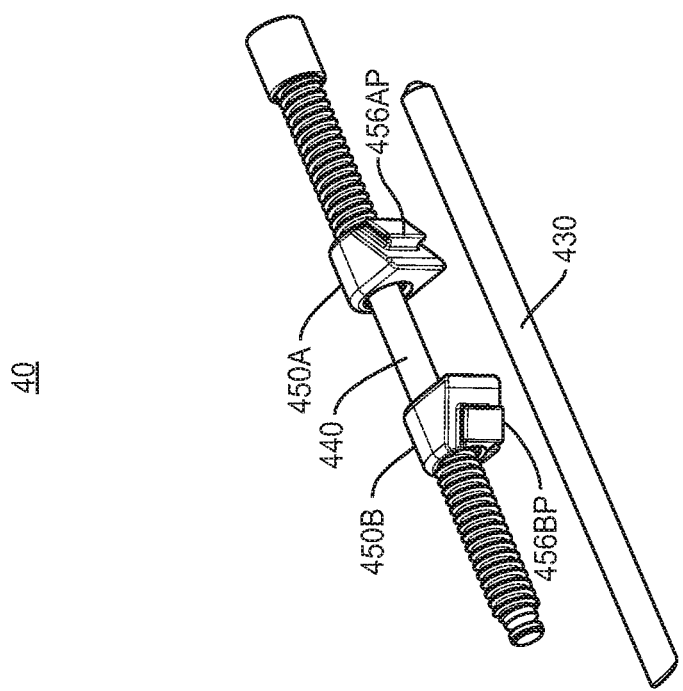
FIG. 29

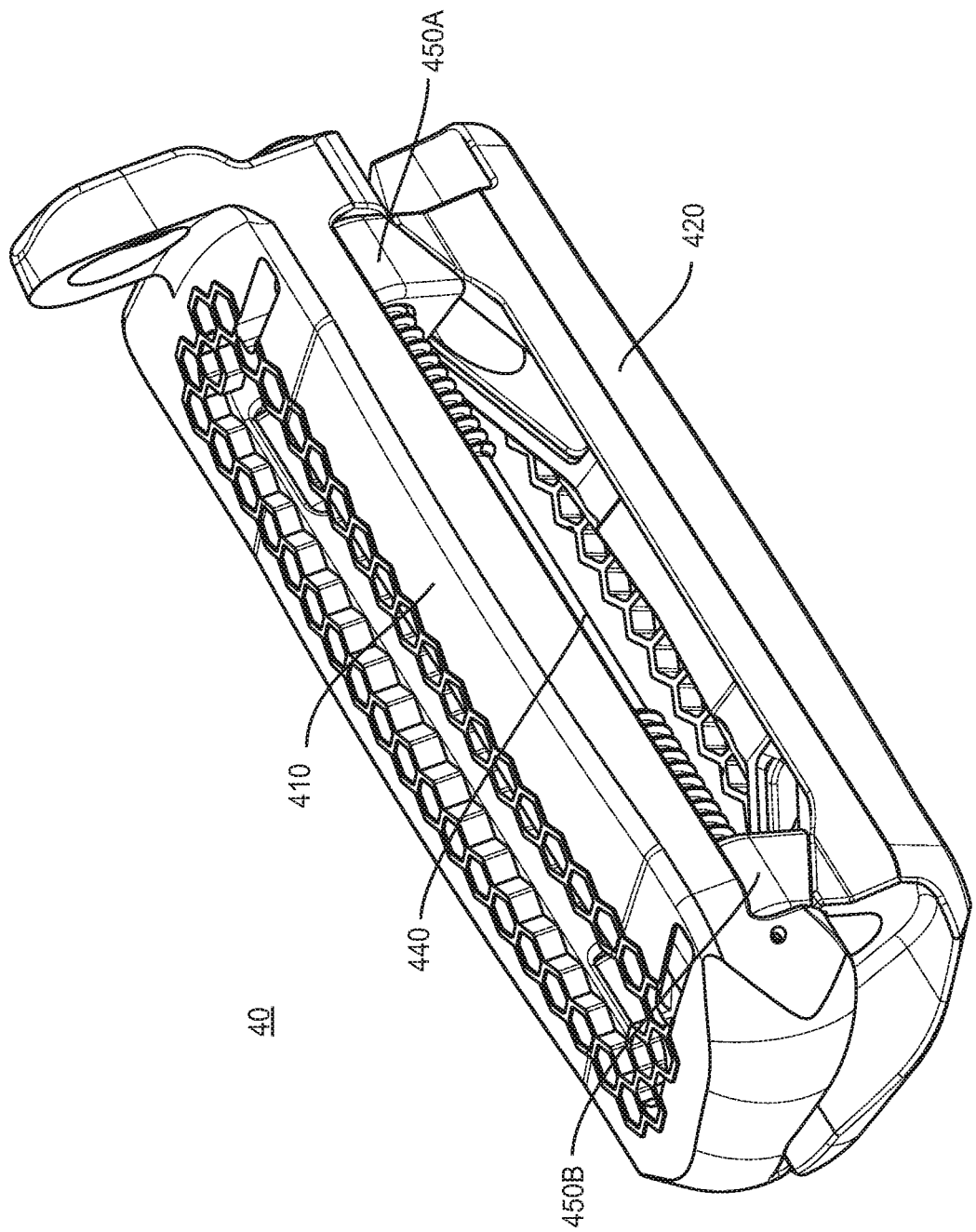

EXPANDABLE SPINAL IMPLANT SYSTEM AND METHOD OF USING SAME

CROSS-REFERENCE TO RELATED U.S. PATENT APPLICATIONS

This Application is a divisional of U.S. patent application Ser. No. 16/282,661, entitled "EXPANDABLE SPINAL IMPLANT SYSTEM AND METHOD OF USING SAME", filed Feb. 22, 2019, the entire content of which is incorporated herein by reference; and claims benefit to U.S. Provisional Patent Application Ser. No. 62/634,033, entitled "EXPANDABLE SPINAL IMPLANT SYSTEM AND METHOD OF USING SAME", filed Feb. 22, 2018, which is incorporated herein by reference in its entirety; and to U.S. Provisional Patent Application Ser. No. 62/652,742 entitled "EXPANDABLE SPINAL IMPLANT SYSTEM AND METHOD OF USING SAME", filed Apr. 4, 2018, which is incorporated herein by reference in its entirety.

TECHNICAL FIELD

The present disclosure generally relates to medical devices for the treatment of musculoskeletal disorders, and more particularly to a surgical system that includes an expandable spinal implant, systems for implanting an expandable spinal implant, and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, interbody devices may be introduced to a space between adjacent vertebral bodies (the interbody space) to properly space the vertebral bodies and provide a receptacle for bone growth promoting materials.

In spinal reconstruction surgery requiring correction of the anterior disc space, non-parallel or high angulation spacers are typically used. These spacers are pre-set and require a high amount of force to place the spacers into the intervertebral space.

A further problem is instability of existing expandable interbody devices as they are expanded. Often, the load-bearing surfaces move relative to one another, as well as relative to an inserter, as the interbody device is expanded such that there is a risk of undesired shifts in the positioning of the interbody device within the intervertebral space.

The present invention seeks to address these and other shortcomings in the existing art.

SUMMARY

In one aspect, the present disclosure provides an expandable spinal implant deployable between a contracted position and an expanded position in a disc space between upper and lower vertebral bodies, the expandable spinal implant comprising a first endplate, the first endplate including an outer surface and an inner surface, a first endplate first end, a first endplate second end, a first endplate first lateral surface extending between the first endplate first end and the first endplate second end, an opposing first endplate second lateral surface extending between the first endplate first end and the first endplate second end; a second endplate, the second endplate including an outer surface and an inner surface, a second endplate first end, a second endplate second end, a second endplate first lateral surface extending between the second endplate first end and the second endplate second end, and an opposing second endplate second lateral surface extending between the second endplate first end and the second endplate second end, wherein the second endplate first end is pivotably engaged with the first endplate first end; an expansion mechanism disposed between the first endplate and the second endplate, the expansion mechanism including a first wedge disposed between the first endplate and second endplate, the first wedge including an upper surface, a lower surface, a first wedge first end, a first wedge second end, a first wedge first lateral surface extending between the first wedge first end and the first wedge second end, and an opposing first wedge second lateral surface extending between the first wedge first end and the first wedge second end, wherein the first wedge comprises a first wedge aperture between the first wedge first lateral surface and opposing first wedge second lateral surface; a second wedge disposed between the first endplate and second endplate, the second wedge including an upper surface, a lower surface, a second wedge first end, a second wedge second end, a second wedge first lateral surface extending between the second wedge first end and the second wedge second end, and an opposing second wedge second lateral surface extending between the second wedge first end and the second wedge second end, wherein the second wedge comprises a second wedge aperture between the second wedge first lateral surface and opposing second wedge second lateral surface; a rod assembly, the rod assembly having a first portion and a second portion, wherein the rod assembly is disposed within the first wedge aperture and second wedge aperture and operably engaged with the first wedge to move the first wedge in a lateral direction and operably engaged with the second wedge to move the second wedge in an opposing lateral direction; wherein the first wedge and second wedge are operably engaged with at least one of the first or second endplate and configured to expand the implant when the first and second wedges are translated along the rod assembly.

In some embodiments, the rod assembly comprises a first threaded outer surface along the first portion and a second threaded outer surface along the second portion, and wherein the first wedge aperture comprises a threaded inner surface operably engaged with the first threaded outer surface of the rod and the second wedge aperture comprises a threaded inner surface operably engaged with the second threaded outer surface of the rod. In some embodiments, wherein the first threaded outer surface and the second threaded outer surface are threaded in opposite directions.

In some embodiments, the expansion mechanism is secured to only one of the first or second endplate to form an endplate expansion mechanism assembly. In some embodiments, the endplate expansion mechanism assembly is configured to urge the endplate that is not secured to the expansion mechanism away from the endplate expansion mechanism assembly when the first and second wedges are moved in a lateral direction. In some embodiments, the lower surfaces of the first and second wedges are configured to urge the second endplate away from the first endplate when the first and second wedges are moved in a medial direction.

In some embodiments, the second endplate further comprises at least one protrusion from its inner surface configured to engage the lower surface of at least one of the first or second wedge. In some embodiments, the at least one protrusion comprises a recess for receiving the rod assembly when the spinal implant is in a closed state. In some embodiments, the first and second sides of the recess are shaped to accommodate translation of the rod assembly as the expandable spinal implant is expanded. In some embodiments, the first endplate comprises at least one aperture into which the at least one protrusion from the inner surface of the second endplate is disposed when the expandable spinal implant is in a closed state.

In some embodiments, the first endplate first lateral surface comprises a first recess and the first endplate opposing lateral surface comprises a second recess, and wherein the lateral ends of the rod assembly are disposed within the first recess and second recess.

In some embodiments, at least one end of the rod assembly comprises a drive interface configured to operably engage with an instrument.

In some embodiments, the first endplate first lateral surface comprises at least one aperture configured to operably engage with an insertion instrument.

In some embodiments, the first endplate first end further comprises at least one protrusion comprising an aperture therethrough extending laterally along the first endplate first end; the second endplate first end further comprises at least one protrusion comprising an aperture therethrough extending laterally along the second endplate first end; and wherein the aperture through the at least one protrusion on the first endplate first end is co-axially aligned with the aperture through the at least one protrusion on the second endplate first end, and wherein a rod is disposed through the apertures to pivotably engage first endplate first end with the second endplate first end.

In some embodiments, at least one of the first or second endplate comprises an aperture disposed therethrough from the outer surface to the inner surface, the aperture configured to receive an external screw for securing the implant to a vertebral body.

In some embodiments, at least one of the first or second endplate comprises a tab extending from a lateral surface, the aperture configured to receive an external screw for securing the implant to a vertebral body.

In some embodiments, at least one of the outer surfaces of the first or second endplates comprise anti-migration features.

In some embodiments, at least one of the first or second endplates comprises at least one aperture between the inner and outer surfaces to allow bone growth material to be loaded into the implant.

Also provided herein is an expandable spinal implant system comprising an insertion instrument; and an expandable spinal implant deployable between a contracted position and an expanded position in a disc space between upper and lower vertebral bodies, the expandable spinal implant comprising a first endplate, the first endplate including an outer surface and an inner surface, a first endplate first end, a first endplate second end, a first endplate first lateral surface extending between the first endplate first end and the first endplate second end, an opposing first endplate second lateral surface extending between the first endplate first end and the first endplate second end; a second endplate, the second endplate including an outer surface and an inner surface, a second endplate first end, a second endplate second end, a second endplate first lateral surface extending between the second endplate first end and the second endplate second end, and an opposing second endplate second lateral surface extending between the second endplate first end and the second endplate second end, wherein the second endplate first end is pivotably engaged with the first endplate first end; an expansion mechanism disposed between the first endplate and the second endplate, the expansion mechanism including a first wedge disposed between the first endplate and second endplate, the first wedge including an upper surface, a lower surface, a first wedge first end, a first wedge second end, a first wedge first lateral surface extending between the first wedge first end and the first wedge second end, and an opposing first wedge second lateral surface extending between the first wedge first end and the first wedge second end, wherein the first wedge comprises a first wedge aperture between the first wedge first lateral surface and opposing first wedge second lateral surface; a second wedge disposed between the first endplate and second endplate, the second wedge including an upper surface, a lower surface, a second wedge first end, a second wedge second end, a second wedge first lateral surface extending between the second wedge first end and the second wedge second end, and an opposing second wedge second lateral surface extending between the second wedge first end and the second wedge second end, wherein the second wedge comprises a second wedge aperture between the second wedge first lateral surface and opposing second wedge second lateral surface; a rod assembly, the rod assembly having a first portion and a second portion, wherein the rod assembly is disposed within the first wedge aperture and second wedge aperture and operably engaged with the first wedge to move the first wedge in a lateral direction and operably engaged with the second wedge to move the second wedge in an opposing lateral direction; wherein the first wedge and second wedge are operably engaged with at least one of the first or second endplate and configured to expand the implant when the first and second wedges are translated along the rod assembly.

Also provided herein is a method of deploying an expandable spinal implant in a disc space between an upper vertebral surface and a lower vertebral surface, the method comprising, utilizing an expandable spinal implant deployable between a contracted or closed position and an expanded or open position in a disc space between upper and lower vertebral bodies, the expandable spinal implant comprising a first endplate, the first endplate including an outer surface and an inner surface, a first endplate first end, a first endplate second end, a first endplate first lateral surface extending between the first endplate first end and the first endplate second end, an opposing first endplate second lateral surface extending between the first endplate first end and the first endplate second end; a second endplate, the second endplate including an outer surface and an inner surface, a second endplate first end, a second endplate second end, a second endplate first lateral surface extending between the second endplate first end and the second endplate second end, and an opposing second endplate second lateral surface extending between the second endplate first end and the second endplate second end, wherein the second endplate first end is pivotably engaged with the first endplate first end; an expansion mechanism disposed between the first endplate and the second endplate, the expansion mechanism including a first wedge disposed between the first endplate and second endplate, the first wedge including an upper surface, a lower surface, a first wedge first end, a first wedge second end, a first wedge first lateral surface extending between the first wedge first end and the first wedge second end, and an opposing first wedge second lateral surface extending between the first wedge first end and the first wedge second end, wherein the first wedge comprises a first wedge aperture between the first wedge first lateral surface and opposing first wedge second lateral surface; a second wedge disposed between the first endplate and second endplate, the second wedge including an upper surface, a lower surface, a second wedge first end, a second wedge second end, a second wedge first lateral surface extending between the second wedge first end and the second wedge second end, and an opposing second wedge second lateral surface extending between the second wedge first end and the second wedge second end, wherein the second wedge comprises a second wedge aperture between the second wedge first lateral surface and opposing second wedge second lateral surface; a rod assembly, the rod assembly having a first portion and a second portion, wherein the rod assembly is disposed within the first wedge aperture and second wedge aperture and operably engaged with the first wedge to move the first wedge in a lateral direction and operably engaged with the second wedge to move the second wedge in an opposing lateral direction; wherein the first wedge and second wedge are operably engaged with at least one of the first or second endplate and configured to expand the implant when the first and second wedges are translated along the rod assembly; inserting the implant in the collapsed position into the disc space between the upper and lower vertebral bodies; and expanding the first and second endplates.

In other aspects of the present disclosure, various other implants, systems and methods are disclosed.

BRIEF DESCRIPTION OF THE DRAWINGS

The present disclosure is further informed by the specific description accompanied by the following drawings, in which:

FIG. 29 is an exploded bottom perspective view of one embodiment of an expandable spinal implant in accordance with the principles of the present disclosure;

FIG. 31 is a perspective view of one embodiment of an open expandable spinal implant in accordance with the principles of the present disclosure;

Figure 1:
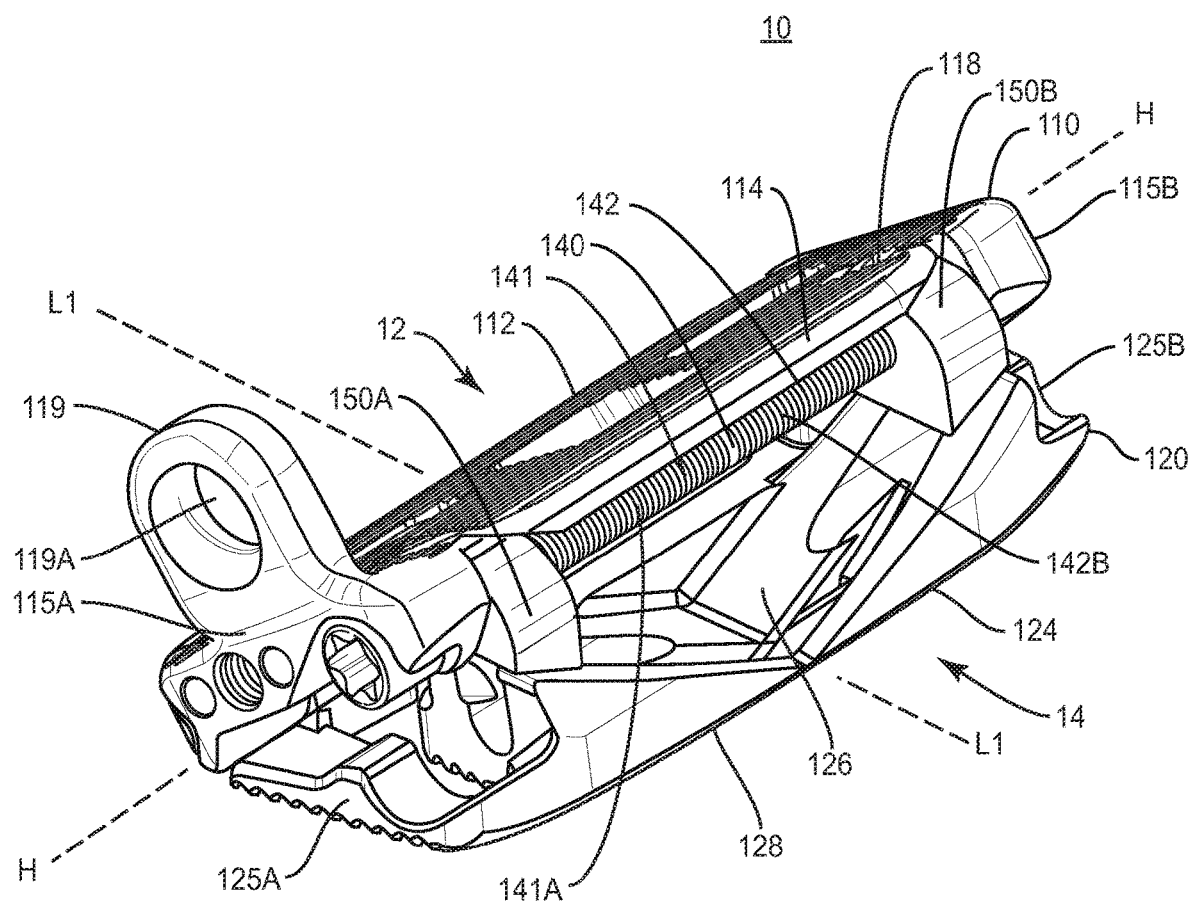
FIG. 1 is a perspective view of one embodiment of an expandable spinal implant in an open configuration in accordance with the principles of the present disclosure.
Figure 2:
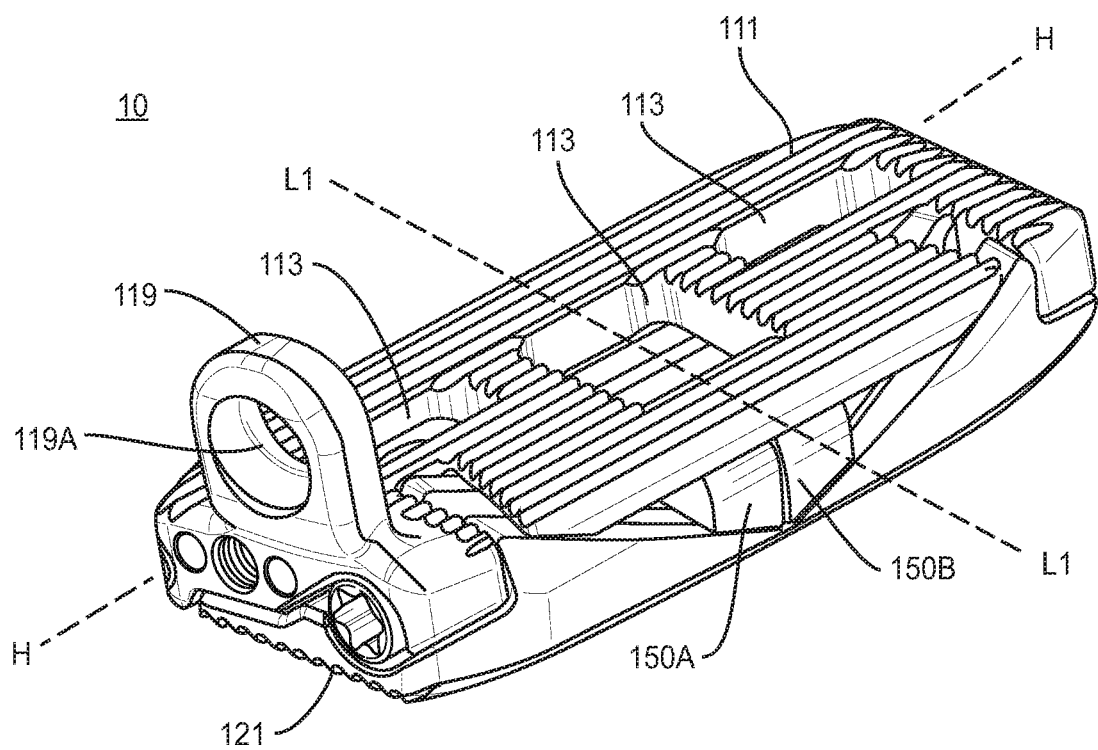
FIG. 2 is a perspective view of one embodiment of an expandable spinal implant in a closed configuration in accordance with the principles of the present disclosure.
Figure 3:
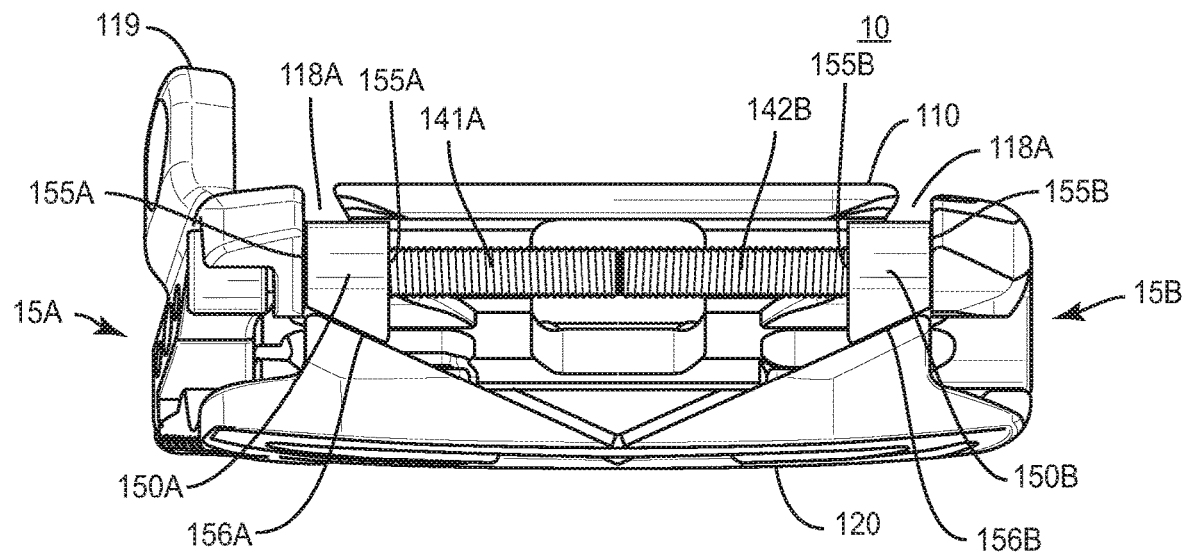
FIG. 3 is an end view of one embodiment of an expandable spinal implant in an open configuration in accordance with the principles of the present disclosure.
Figure 4:
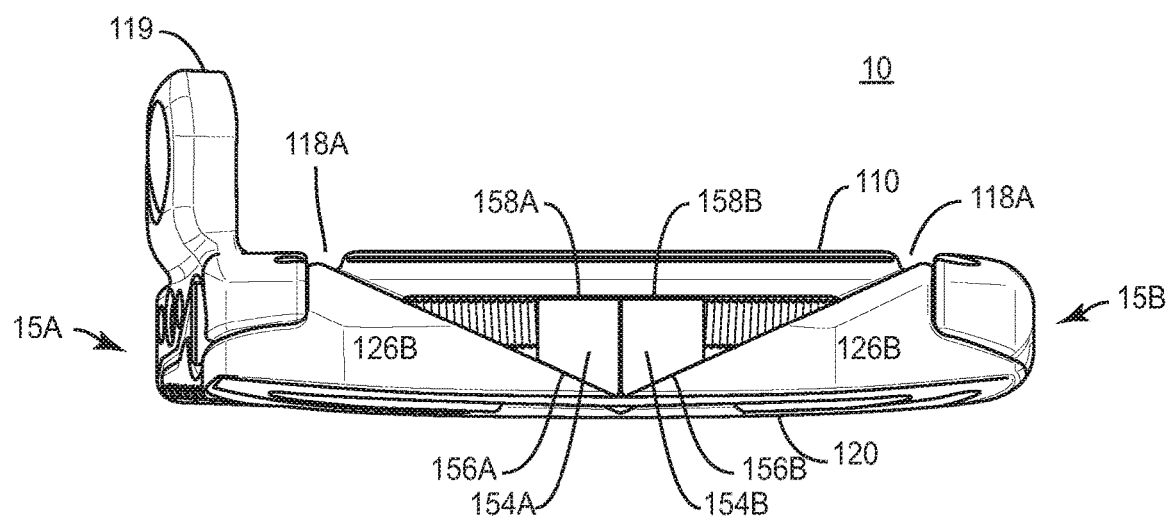
FIG. 4 is an end view of one embodiment of an expandable spinal implant in an closed configuration in accordance with the principles of the present disclosure.
Figure 5:
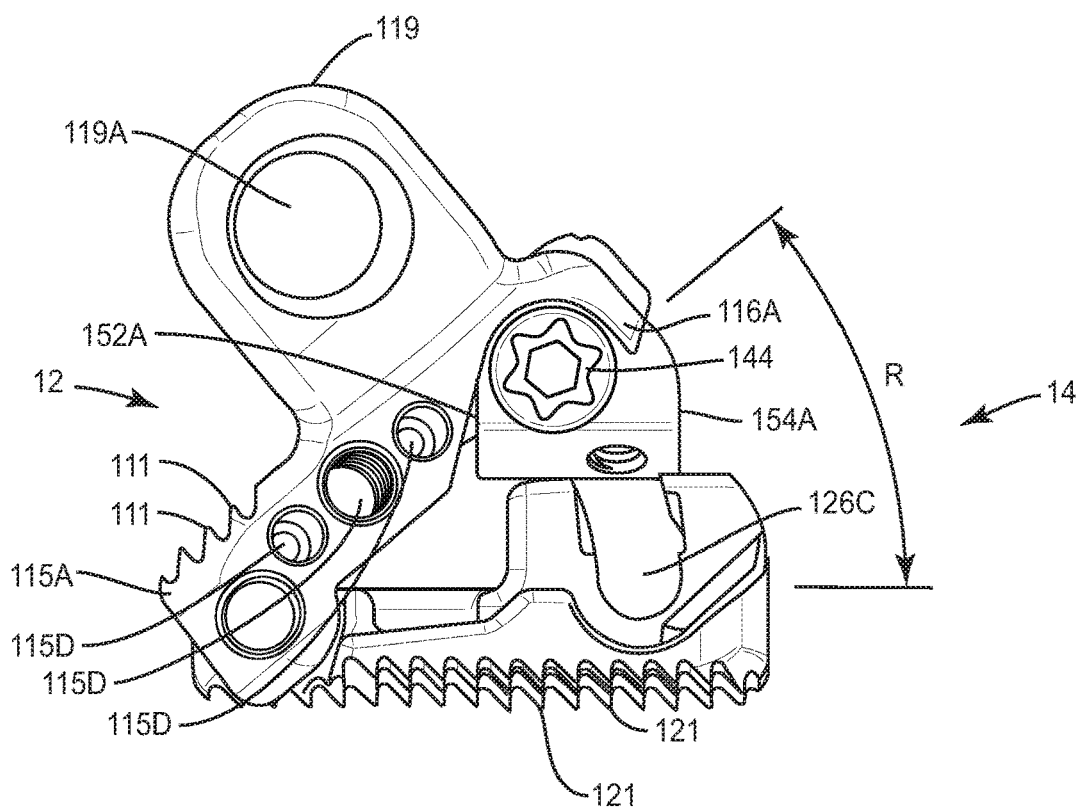
FIG. 5 is a side end view of one embodiment of an expandable spinal implant in an open configuration in accordance with the principles of the present disclosure.
Figure 6:
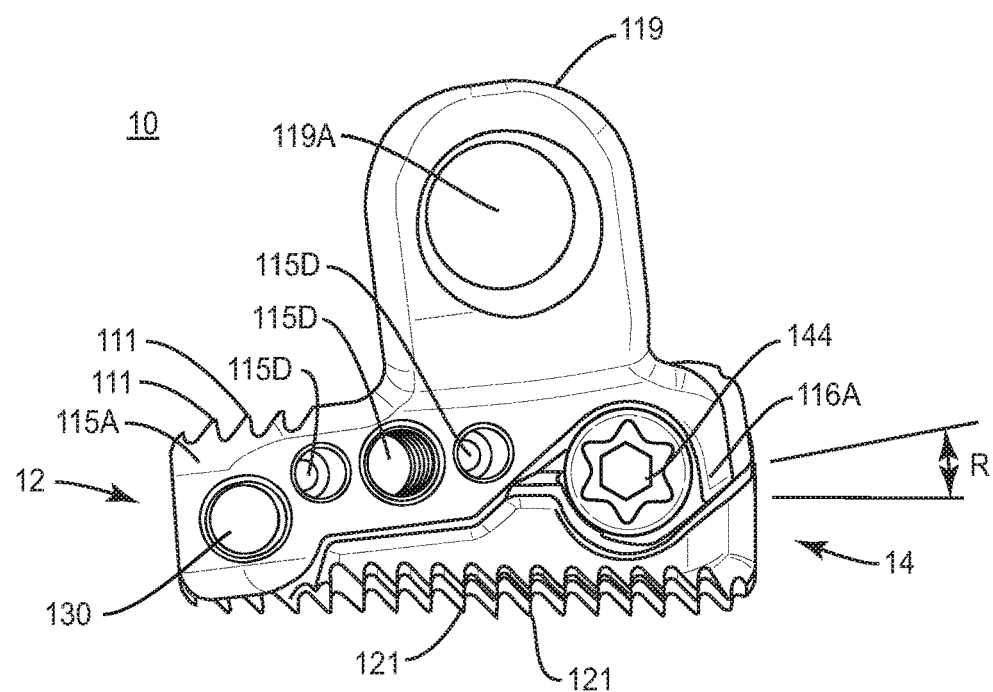
FIG. 6 is a side end view of one embodiment of an expandable spinal implant in a closed configuration in accordance with the principles of the present disclosure.

Common numbering schemes in FIGS. 1-34 (e.g., 1xx, 2xx, 3xx, 4xx), indicate similar components of implants 10, 20, 30, and 40.

DETAILED DESCRIPTION

The exemplary embodiments of the surgical system and related methods of use disclosed are discussed in terms of medical devices for the treatment of musculoskeletal disorders and more particularly, in terms of an expandable surgical implant system that may include an expandable spinal implant, an insertion instrument, specialized instruments such as, for example, an expandable retractor and a spinal surgical table that rotates and bends the patient in various directions, and/or a method or methods for treating a spine.

In some embodiments, the present system includes an expandable spinal implant suitable for insertion via various spinal procedures, in particular a direct lateral interbody fusion (sometimes referred to as DLIF procedures), and oblique lateral interbody fusion (sometimes referred to as OLIF procedures). Other procedures contemplated for use with expandable implant systems of the present disclosure include postero-lateral procedures and/or transforaminal lumbar interbody fusions (sometimes referred to as TLIF procedures), direct posterior lumbar (sometimes referred to as PLIF procedures), anterior lumbar interbody fusions (sometimes referred to as ALIF procedures), or variations of these procedures, in which the present implant is inserted into an intervertebral space and then expanded in order to impart and/or augment a lordotic and/or kyphotic curve of the spine.

In some embodiments, the spinal implant system may also be employed to restore and/or impart sagittal balance to a patient by increasing and/or restoring an appropriate lordotic and/or kyphotic angle between vertebral bodies at a selected level where the spinal implant is implanted and expanded. In the various embodiments described, the spinal implant system may be useful in a variety of complex spinal procedures for treating spinal conditions beyond one-level fusions. Furthermore, the spinal implant system described in the enclosed embodiments may also be used as a fusion device with an expandable height for tailoring the implant to a particular interbody disc space to restore the spacing between adjacent vertebral bodies and facilitate spinal fusion between the adjacent vertebral bodies.

In some embodiments, and as mentioned above, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral oblique, and/or antero lateral oblique approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components, e.g., a "first end" of an end plate and a "first end" of a wedge, indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

As used in the specification and including the appended claims, "treating" or "treatment" of a disease or condition refers to performing a procedure that may include administering one or more drugs, biologics, bone grafts (including allograft, autograft, xenograft, for example) or bone-growth promoting materials to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise. The term "bone growth promoting material" as used herein may include, but is not limited to: bone graft (autograft, allograft, xenograft) in a variety of forms and compositions (including but not limited to morselized bone graft); osteoinductive material such as bone morphogenetic proteins (BMP) (including but not limited to INFUSE® available from Medtronic) and alternative small molecule osteoinductive substances; osteoconductive materials such as demineralized bone matrix (DBM) in a variety of forms and compositions (putty, chips, bagged (including but not limited to the GRAFTON® family of products available from Medtronic); collagen sponge; bone putty; ceramic-based void fillers; ceramic powders; and/or other substances suitable for inducing, conducting or facilitating bone growth and/or bony fusion of existing bony structures. Such bone growth promoting materials may be provided in a variety of solids, putties, liquids, colloids, solutions, or other preparations suitable for being packed or placed into or around the various implant 10, 20, 30, 40 embodiments described herein.

The following discussion includes a description of a surgical system including one or more spinal implants, related components and methods of employing the surgical system in accordance with the principles of the present disclosure. Various alternate embodiments are disclosed and individual components of each embodiment may be used with other embodiments. Reference is made in detail to the exemplary embodiments of the present disclosure, which are illustrated in the accompanying figures. Turning to FIGS. 1-34, there are illustrated components of a surgical system, such as, for example, an expandable spinal implant 10, 20, 30, and 40.

The components of the expandable spinal implant and system described herein can be fabricated from biologically acceptable materials suitable for medical applications, including metals, synthetic polymers, ceramics and bone material and/or their composites. For example, the components of expandable spinal implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system may be formed or constructed material composites, including the above materials, to achieve various desired characteristics such as strength, rigidity, elasticity, compliance, biomechanical performance, durability and radiolucency or imaging preference. The components of the present expandable spinal implant system, individually or collectively, may also be fabricated from a heterogeneous material such as a combination of two or more of the above-described materials. The components of the expandable spinal implant system may be monolithically formed, integrally connected or include fastening elements and/or instruments, as described herein. For example, in some embodiments the expandable spinal implant system may comprise expandable spinal implants 10, 20, 30, 40 comprising PEEK and/or titanium structures with radiolucent markers (such as tantalum pins and/or spikes) selectively placed in the implant to provide a surgeon with placement and/or sizing information when the expandable spinal implant 10, 20, 30, 40 is placed in the spine. The components of expandable spinal implant system may be formed using a variety of subtractive and additive manufacturing techniques, including, but not limited to machining, milling, extruding, molding, 3D-printing, sintering, coating, vapor deposition, and laser/beam melting. Furthermore, various components of the expandable spinal implant system may be coated or treated with a variety of additives or coatings to improve biocompatibility, bone growth promotion or other features. For example, the endplates 110, 120, 210, 220, 310, 320, 410, 420 may be selectively coated with bone growth promoting or bone ongrowth promoting surface treatments that may include, but are not limited to: titanium coatings (solid, porous or textured), hydroxyapatite coatings, or titanium plates (solid, porous or textured).

The expandable spinal implant system may be employed, for example, with a minimally invasive procedure, including percutaneous techniques, mini-open and open surgical techniques to deliver and introduce instrumentation and/or one or more spinal implants at a surgical site within a body of a patient, for example, a section of a spine. In some embodiments, the expandable spinal implant system may be employed with surgical procedures, as described herein, and/or, for example, corpectomy, discectomy, fusion and/or fixation treatments that employ spinal implants to restore the mechanical support function of vertebrae. In some embodiments, the expandable spinal implant system may be employed with surgical approaches, including but not limited to: anterior lumbar interbody fusion (ALIF), direct lateral interbody fusion (DLIF), oblique lateral lumbar interbody fusion (OLLIF), posterior lumbar interbody fusion (PLIF), oblique lateral interbody fusion (OLIF), transforaminal lumbar interbody fusion (TLIF), various types of anterior fusion procedures, and any fusion procedure in any portion of the spinal column (sacral, lumbar, thoracic, and cervical, for example).

Generally in FIGS. 1-34, four exemplary embodiments of an expandable spinal implant 10, 20, 30, and 40 are shown (implant 10 is highlighted in exemplary FIGS. 1-9, implant 20 is highlighted in exemplary FIGS. 10-17, implant 30 is highlighted in exemplary FIGS. 18-24, and implant 40 is highlighted in exemplary FIGS. 25-34). Expandable spinal implants 10, 20, 30, and 40 may comprise first and second endplates operably engaged via a first end hinge mechanism, pin mechanism, protrusion/channel mechanism or similar connections that lordotically or angularly expands the endplates relative to one another via a wedge mechanism driven parallel to the axis of the first end. In some embodiments, the wedge drive direction may be oriented at an oblique angle between 0 and 90 degrees relative to the first end.

As shown in FIGS. 1-9, an expandable spinal implant 10 is configured to be inserted in an intervertebral disc space between an upper vertebral body and an adjacent lower vertebral body. The implant 10 includes a first end 12 and a second end 14 defining a mid-longitudinal axis L1-L1 therebetween. Implant 10 also includes a lateral side 15A and an opposing lateral side 15B. In some embodiments, the expandable spinal implant 10 comprises a first endplate 110 and second endplate 120. First endplate 110 includes a first end 112, a second end 114, a first side surface 115A and an opposing second side surface 115B, an inner surface 116, and an outer surface 118. Second endplate 120 includes a first end 122, a second end 124, a first side surface 125A and an opposing second side surface 125B, an inner surface 126, and an outer surface 128. In one embodiment, the endplates 110, 120 includes projections 111, 121 configured to engage a surface of the endplate of the adjacent vertebral body (not shown). Projections 111, 121 may comprise various anti-migration, anti-expulsion, and/or osseointegration features including, but not limited to: ridges, teeth, pores, and coatings (including but not limited to porous titanium coatings such as those provided on Capstone PTC™ implants available from Medtronic). The endplates 110, 120 may further comprise at least one opening 113, 123 defined therein, configured to allow bone growth materials to be packed, placed, or loaded into the implant 10.

Figure 7:
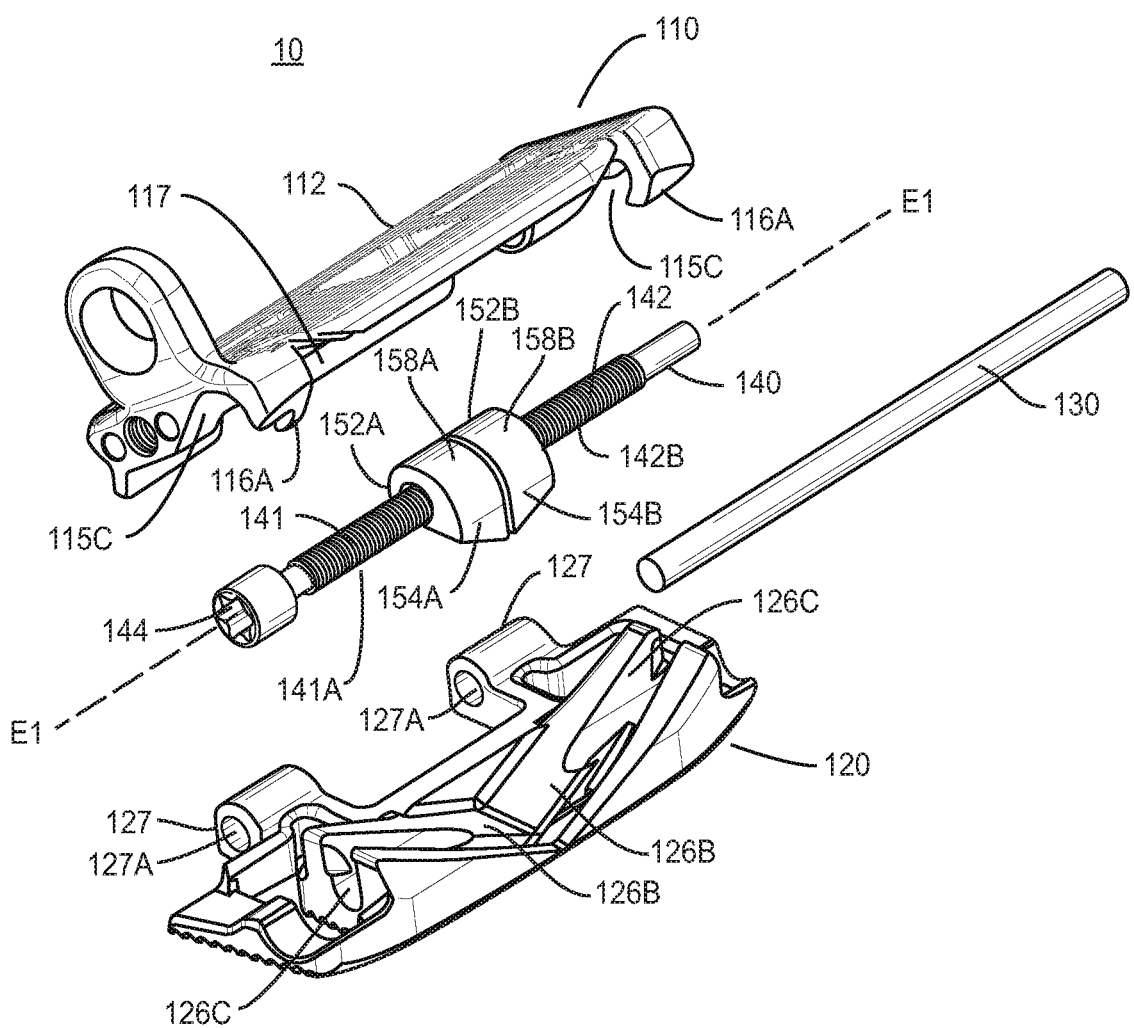
FIG. 7 is a first exploded perspective view of one embodiment of an expandable spinal implant in accordance with the principles of the present disclosure.
Figure 8:
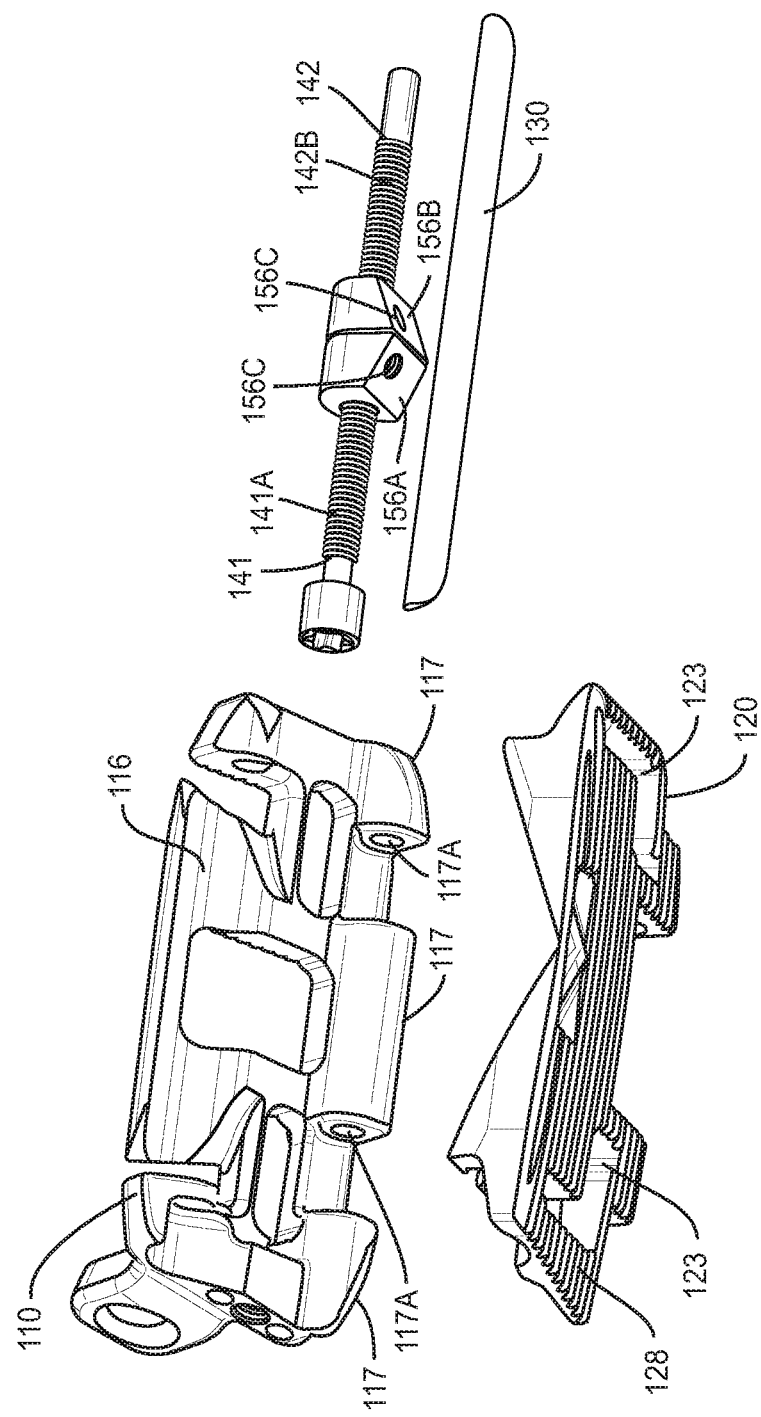
FIG. 8 is a second exploded perspective view of one embodiment of an expandable spinal implant in accordance with the principles of the present disclosure.
Figure 9:
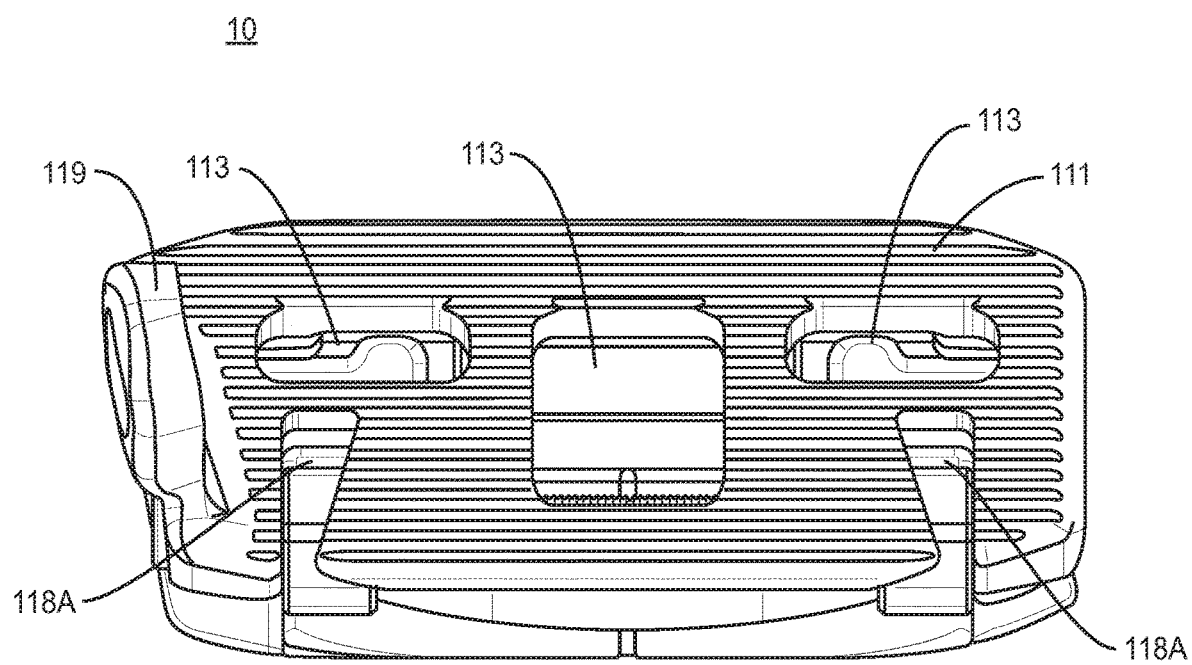
FIG. 9 is a top view of one embodiment of an expandable spinal implant in an open configuration in accordance with the principles of the present disclosure.
Figure 10:
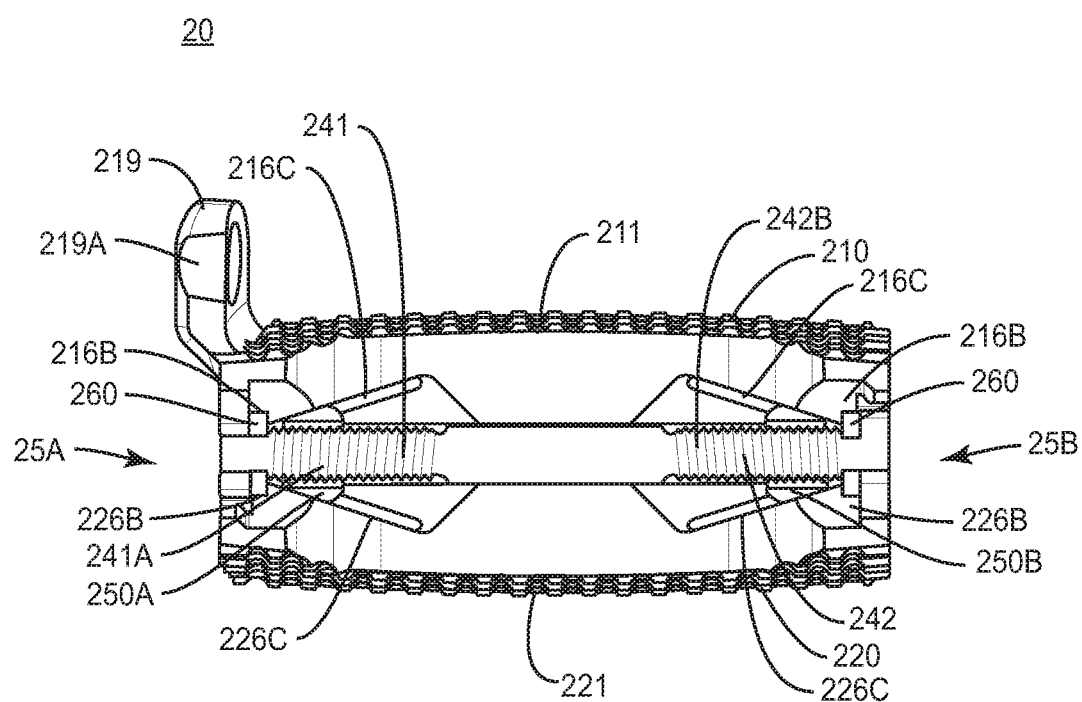
FIG. 10 is a cutaway end view of one embodiment of an expandable spinal implant in an open configuration in accordance with the principles of the present disclosure.
Figure 11:
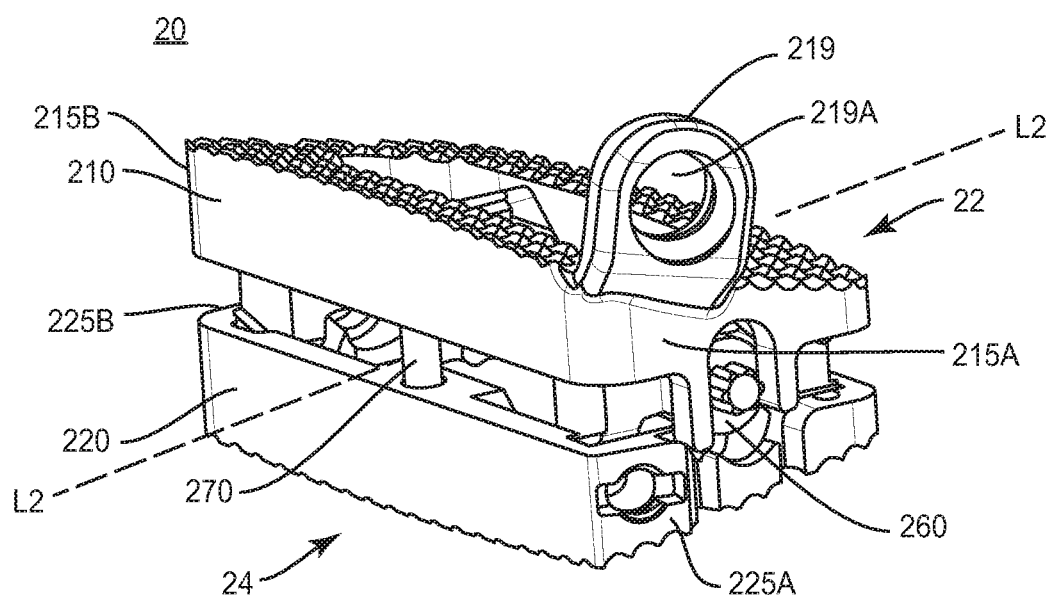
FIG. 11 is a perspective view of one embodiment of an expandable spinal implant in an open configuration in accordance with the principles of the present disclosure.
Figure 12:
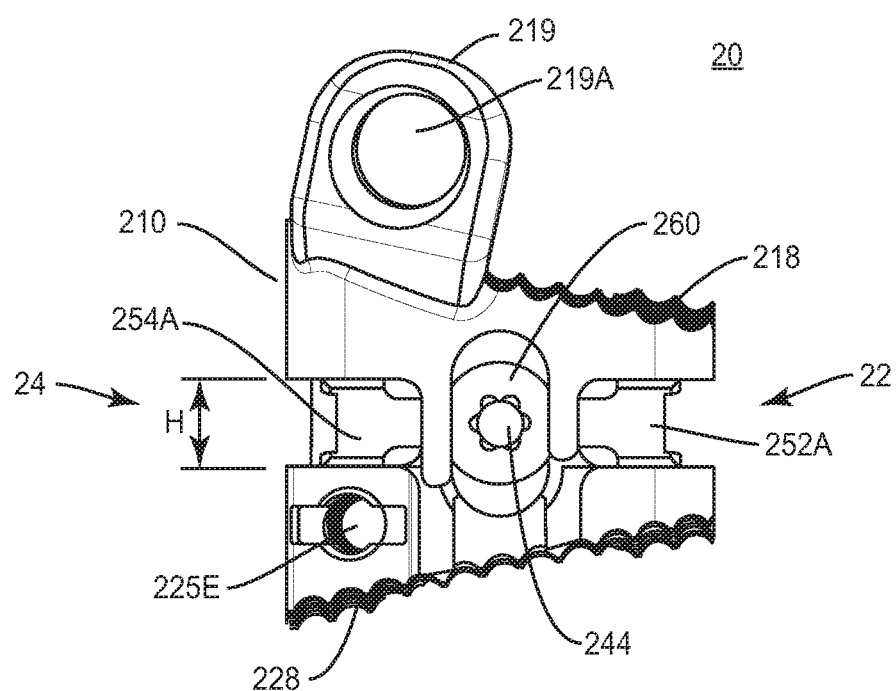
FIG. 12 is a side end view of one embodiment of an expandable spinal implant in an open configuration in accordance with the principles of the present disclosure.

Referring generally to FIGS. 1-9, the endplates 110, 120 may be operably engaged via a hinge mechanism located near or on the first ends 112 and 122. For example, as shown in FIG. 8, first end 112 of first endplate 110 may comprise hinge protrusions 117 extending along at least a portion of the length of first end 112 perpendicular to mid-longitudinal axis L1-L1 and further comprising lumens 117a extending therethrough. First end 122 of second endplate 120 may also comprise similar hinge protrusions 127, as shown in FIG. 7. In some embodiments, hinge protrusions 127 are cylindrical and extend laterally along at least a portion of the length of first end 122 perpendicular to mid-longitudinal axis L1-L1, and further comprise lumens 127a extending therethrough. The lumen of hinge protrusions 117 and lumen of hinge protrusions 127 may be co-axially aligned along a hinge axis H-H. A pin 130 may be disposed within the lumen 117a, 127a of hinge protrusions 117, 127 to operably engage first endplate 110 to second endplate 120. In this way, first endplate 110 may hinge and/or rotate away from second endplate 120 such that the distance between second ends 114 and 124 is increased along radial arc R. While a simple pin and lumen hinge is shown in some of the pictured embodiments, it should be understood that other types of hinge and/or connection mechanisms might also be used to operably engage the endplates 110, 120 of the implant. For example, in some embodiments, a "living hinge" may be utilized wherein the endplates 110, 120 are at least partially integrally formed at the hinge point but with cut-outs or flex points that allow the endplates 110, 120 to rotate about the hinge connection. In summary, the endplates 110, 120 may be operably engaged in a number of different ways including but not limited to: integral connections, separable connections, mechanically fixed connections using fastener or adhesives, releasable connections (including, but not limited to keyways and partially open hinges), and other connection types. In some embodiments, the endplates 110, 120 may be integrally formed using additive manufacturing techniques such as 3D printing, sintering laser/beam melting, casting, extruding, or machined in an integral form using subtractive manufacturing techniques from one or more stock materials.

As described herein, the implant 10 may include an expansion mechanism for lordotically expanding the endplates 110, 120. The expansion mechanism may be disposed within the implant between the first endplate 110 and second endplate 120. In some embodiments, the expansion mechanism of implant 10 includes a rod assembly 140. Rod assembly 140 has a longitudinal axis E1-E1 and may comprise a first portion 141 and a second portion 142. In some embodiments, rod assembly 140 may be integrally formed, or may be formed of multiple components for, e.g., ease of manufacturing and/or assembly. In some embodiments, the expansion mechanism comprises a first wedge 150A and a second wedge 150B. Each of first and second wedges 150A and 150B may comprise first ends 152A and 152B, second ends 154A and 154B, upper surfaces 158A and 158B, lower surfaces 156A and 156B, and lateral surfaces 155A and 155B extending between the first ends 152A and 152B and the second ends 154A and 154B. The first wedge 150A may further comprise a first wedge aperture 151A between the lateral surfaces 155A and the second wedge 150B may further comprise a second wedge aperture 151B between lateral surfaces 155B. The rod assembly 140 may be disposed within the first and second apertures. In some embodiments, the rod first portion 141 comprises a threaded outer surface 141A configured to be engaged with complimentary inner threaded surface of the first aperture 151A of first wedge 150A such that the first wedge 150A travels laterally along rod assembly 140 when the rod assembly 140 is rotated relative to the first wedge 150A. In some embodiments, the rod second portion 142 comprises a threaded outer surface 142B configured to be engaged with complimentary inner threaded surface of the second aperture 151B of second wedge 150B such that the second wedge 150B travels laterally along rod assembly 140 when the rod assembly 140 is rotated relative to the second wedge 150B. The first and second threaded surfaces may have opposite pitches such that first wedge 150A and second wedge 150B translate in opposing lateral directions when rod assembly 140 is rotated relative to first and second wedges 150A and 150B. In some embodiments, the rod assembly 140 and first and second wedges 150A and 150B may be operably engaged such that first and second wedges 150A and 150B translate in the same lateral direction when rod assembly 140 is rotated relative to first and second wedges 150A and 150B.

The expansion mechanism of implant 10 may be operably engaged with the first or second endplates 110, 120. In some embodiments, the expansion mechanism of implant 10 is secured to first endplate 110. Inner surface 116 of first endplate 110 may comprise protrusions 116A defining recesses 115C in first and second lateral ends 115A, 115B in which rod assembly 140 may be secured. Rod assembly 140 may be rotatable within recesses 115C about rod assembly longitudinal axis E1-E1. In some embodiments, the recesses 115C may be aligned such that longitudinal axis L of rod assembly 140 is substantially parallel to hinge axis H-H. In other embodiments, the longitudinal axis L of rod assembly 140 may be disposed at an angle oblique to the hinge axis H-H (e.g., between zero and 90 degrees).

First and second wedges 150A, 150B may include lower surfaces 156A, 156B configured to engage with inner surface 126 of second endplate 120 and lordotically expand first endplate 110 away from second endplate 120 when first and second wedges 150A, 150B are moved in a lateral direction. For example, the lower surfaces 156A, 156B may be ramped or wedge-shaped and suitable for urging a complementary ramped or contoured surface on the inside of second endplate 120 so as to gradually move the first endplate 110 away from the second endplate 120 as the first and second wedges 150A, 150B are advanced laterally along the rod assembly 140. In the embodiment depicted, inner surface 126 of second endplate 120 may further comprise ramps 126B to engage lower surfaces 156A, 156B of wedges 150A, 150B. In some embodiments, a portion, or the entire width of the upper surfaces 158A and 158B of wedges 150A, 150B, opposite lower surfaces 156A, 156B may be substantially parallel to the plane of the first endplate 110 rather than wedged or angled relative to the planes of first and/or second endplates 110, 120 and/or may be curved and flat. In some embodiments, the upper surfaces 158A and 158B of wedges 150A, 150B do not operably engage the inner surface 116 of first endplate 110, i.e., do not provide any expansive force to move first endplate 110 relative to the expansion mechanism. In the depicted embodiment, the expansion mechanism comprised of rod assembly 140 and wedges 150A and 150B is secured to first endplate 110 such that the expansion mechanism maintains its relative positioning with respect to the first endplate 110 during expansion. The increase in lordotic angle is accomplished through engagement of the lower surfaces 156A, 156B of wedges 150A, 150B with inner surface 126 of second endplate 120 such that second endplate 120 moves relative to the first endplate 110 and the expansion mechanism assembly. In some embodiments, lower surfaces 156A, 156B of wedges 150A, 150B may comprise apertures 156C for receiving a pin or screw (not shown). The head of the pin or screw may engage with ramps 126B. In some embodiments, ramps 126B may further comprise recesses 126C to receive the rod assembly 140 when the implant 10 is in a closed or partially-expanded state. The sides of the recess are curved or angled to accommodate translation of the rod assembly towards the first end 12 of implant 10 as the implant is expanded and the second endplate is urged away from the first endplate and expansion mechanism secured thereto. The first endplate 110 may also comprise apertures 118A to receive the ramps 126B when the implant 10 is in a closed or partially-expanded state. Such recesses allow for a thinner implant in a closed state while maintaining a large expansion range.

In some embodiments, first and second wedges 150A, 150B may be positioned medially when implant 10 is in a closed state and travel laterally towards sides 115A, 115B to expand implant 10. In other embodiments, first and second wedges 150A, 150B may be positioned laterally when implant 10 is in a closed state and travel medially towards mid-longitudinal axis L1-L1 to expand implant 10. In some embodiments, various designs may be used to optimize the interaction of the first and second wedges 150A, 150B with the first end plate 110 and/or the second endplate 120. Such configurations may include, but are not limited to: sequential ramps or tapered surfaces with varying angles; shallow angle sequential ramps or tapered surfaces leading into higher angle sequential ramps or tapered surfaces, as well as other opening mechanisms (such as the lateral post and channel system as described in, e.g., U.S. Provisional Patent Application Ser. No. 62/633,952 (hereinafter the "952 application"), incorporated herein by reference in its entirety).

To supplement the expansion force of the device, this device can be specifically paired with other surgical instruments that manipulate the spine. These surgical instruments may include, for example, surgical tables, patient positioning frames, and the like, that manipulate the patient and may for example further facilitate and/or adjust access to one or more disc spaces by bending the patient spine in various directions and adjust the orientation of the patient to ease or facilitate access to the spinal surgical location(s). Exemplary surgical tables, patient positioning frames, and the like, and related methods of using them include those described in, e.g., U.S. patent application Ser. Nos. 15/239,239, 15/239, 256, 15/337,157, 15/638,802, 15/639,080, 15/672,005, and 15/674,456, all incorporated herein by reference in their entirety.

In some embodiments, one or both ends of rod assembly 140 may comprise an interface 144 configured to be operably engaged by a drive shaft (not shown) to rotate the rod 140. The rod interface 144 may comprise a drive receptacle configured to cooperate with an implant-engaging end of the drive shaft. The drive connection between the driver shaft and the rod interface 144 may comprise a variety of drive interfaces including but not limited to: multi-lobular drives; hexalobular drives; cross or Phillips head drives; straight or "flat head" drives; square or other polygonal drives; and/or combinations thereof.

In some embodiments, implant 10 may be secured through various mechanisms to the adjacent vertebral bodies. In some embodiments, the first or second endplates 110, 120 may comprise a tab or separable plate through which a screw may be disposed. In the depicted embodiment, first endplate 110 may comprise a tab 119 comprising an aperture 119A through which a screw (not shown) may be disposed to secure endplate 110 within an intervertebral space. In some embodiments, tab 119 may not be present on implant 10, or one or more additional tabs may be present on first and/or second endplates 110, 120. Contemplated screws may comprise a threaded outer surface that engages with the inner surface of aperture 119A, which may also be threaded. The engagement between the threaded screw outer surface and the inner surface of aperture 119A may be via pitch lock, major/minor lock, or any other thread/pitch interface. In other embodiments, implant 10 may be secured through intrinsic screws placed through apertures between inner surfaces 116, 126 and outer surfaces 118, 128 of endplates 110 or 120 or separable plates that may cover and/or be attached to a portion of the intervertebral implant. One or more of these screws (individually or simultaneously) may be retained by various anti-backout mechanisms such as pins, springs, movable plates or similar mechanisms to push against a portion of the screw and/or cover a portion of the screw hole after insertion of the screw. In other embodiments, implant 10 may comprise one or more engagement components that may be retracted within the device to allow for easy insertion into the disc space when implant 10 is in a closed or unexpanded state, and which may protrude from the outer surfaces 118, 128 of first and/or second endplates 110, 120 during expansion to engage the vertebral endplate(s) to prevent or decrease potential migration or expulsion of the device from the intervertebral space. Exemplary engagement mechanisms are described in, e.g., the 952 application, incorporated herein by reference in its entirety.

Implant 10 may be further configured to operably engage with an insertion instrument (not shown) using a variety of mechanisms. In the depicted embodiment, lateral side 115A of first endplate 110 comprises attachment apertures 115D, although similar apertures are contemplated in second endplate 120 as well. These apertures 115D may be spaced and angled relative to hinge axis H-H of implant 10 as desired for particular surgical techniques. In some embodiments, the apertures 115D may be parallel to hinge axis H-H of implant 10. In other embodiments, the axis of apertures 115D is angled at approximately 15 degrees relative to hinge axis H-H. In some embodiments, the axis of apertures 115D may be offset relative to each other, i.e., the central aperture may be parallel to hinge axis H-H while one or both of the lateral apertures may be angled at, e.g., approximately 15 degrees relative to hinge axis H-H. Apertures 115D may comprise an inner threaded surface for engaging the threaded outer surface on an implant-engaging end of an insertion instrument. In other embodiments, the implant-engaging end of the insertion instrument may interact with tabs or slots defined by one or both of endplates 110, 120.

FIGS. 10-17 show various configurations of an implant 20 according to the present disclosure to provide parallel expansion to increase the height of the device while maintain a constant lordotic angle. Implant 20 has a first end 22 and a second end 24 and lateral sides 25A and 25B therebetween and is generally similar in construction to implant 10 discussed above and implant 30 discussed below, and comprises a first endplate 210 and second endplate 220 operably engaged to an expansion mechanism comprising a rod assembly 240 and first and second wedges 250A, 250B disposed therebetween. First endplate 210 includes a first end 212, a second end 214, a first side surface 215A and an opposing second side surface 215B, an inner surface 216, and an outer surface 218. Second endplate 220 includes a first end 222, a second end 224, a first side surface 225A and an opposing second side surface 225B, an inner surface 226, and an outer surface 228. In one embodiment, the endplates 210, 220 includes projections 211, 221 configured to engage a surface of the endplate of the adjacent vertebral body (not shown). Projections 211, 221 may comprise various antimigration, anti-expulsion, and/or osseointegration features including, but not limited to: ridges, teeth, pores, and coatings (including but not limited to porous titanium coatings such as those provided on Capstone PTC™ implants available from Medtronic). The endplates 210, 220 may further comprise at least one opening 213, 223 defined therein, configured to allow bone growth materials to be packed, placed, or loaded into the implant 20. However, unlike implant 10, the first end 212 of first endplate 210 and the first end 222 of second endplate 220 are not operably engaged such that the entire first endplate 210 may expand away from second endplate 220. In some embodiments, the first and second ends 212, 214 of first endplate 210 (and the rest of the endplate therebetween) expand at the same rate such that the lordotic angle (e.g., zero degrees to 45 degrees) of the implant 20 remains constant while the height H of the device increases.

The expansion mechanism (comprised of rod assembly 240 and wedges 250A and 250B) is designed to expand first endplate 210 and second endplate 220 away from each other as wedges 250A, 250B are translated laterally along rod assembly 240. Rod assembly 240 has a longitudinal axis E2-E2 and may comprise a first portion 241 and a second portion 242. In some embodiments, the rod first portion 241 comprises a threaded outer surface 241A configured to be engaged with complimentary inner threaded surface of a first aperture 251A of first wedge 250A such that the first wedge 250A travels laterally along rod assembly 240 when the rod assembly 240 is rotated relative to the first wedge 250A. In some embodiments, the second rod portion 242 comprises a threaded outer surface 242B configured to be engaged with complimentary inner threaded surface of the second aperture 251B of second wedge 250B such that the second wedge 250B travels laterally along rod assembly 240 when the rod assembly 240 is rotated relative to the second wedge 250B. In some embodiments, rod assembly 240 may be integrally formed, or may be formed of multiple components for, e.g., ease of manufacturing and/or assembly. First wedge 250A may comprise a first end 252A and a second end 254A. Similarly, second wedge 250B may comprise a first end 252B and a second end 254B. In some embodiments, the upper and/or lower surfaces of wedge first ends 252A, 252B and wedge second ends 254A, 254B may be ramped or wedge-shaped and suitable for urging complementary ramped or contoured surfaces on the inside of endplates 210, 220 so as to gradually move the endplates 210, 220 away from each other as the wedges 250A, 250B are advanced laterally along the rod assembly 240. In some embodiments, first and second wedges 250A, 250B may be positioned medially when implant 20 is in a closed state and travel laterally towards the sides to expand implant 20. In other embodiments, first and second wedges 250A, 250B may be positioned laterally when implant 20 is in a closed state and travel medial towards mid-longitudinal axis L2-L2 to expand implant 20. In some embodiments, the expansion mechanism 240, 250A, 250B may be positioned centrally between the first and second ends of implant 20 with its axis generally perpendicular to axis L2-L2 of implant 20. In some embodiments, the expansion mechanism comprises washers 260 that engage internal recesses 216B, 226B within the first and second endplates 210, 220 to keep the expansion mechanism positioned centrally within the device. In other embodiments, the longitudinal axis E2-E2 of expansion mechanism 240, 250A, 250B may be positioned towards first or second ends 22, 24 of implant 20, and/or its axis may be angled obliquely to longitudinal axis L2-L2.

As described above for implant 10, one or both ends of rod assembly 240 may comprise an interface 244 configured to be operably engaged by a driver instrument 40 to rotate the rod assembly 240. The driver instrument 40 may comprise a handle 41, a drive shaft 42, and an implant-engaging end 43. The rod interface 244 may comprise a drive receptacle configured to cooperate with implant-engaging end 43 of the driver instrument. The drive connection between the driver instrument and the rod interface 244 may comprise a variety of drive interfaces including but not limited to: multi-lobular drives; hexalobular drives; cross or Phillips head drives; straight or "flat head" drives; square or other polygonal drives; and/or combinations thereof.

Figure 13:
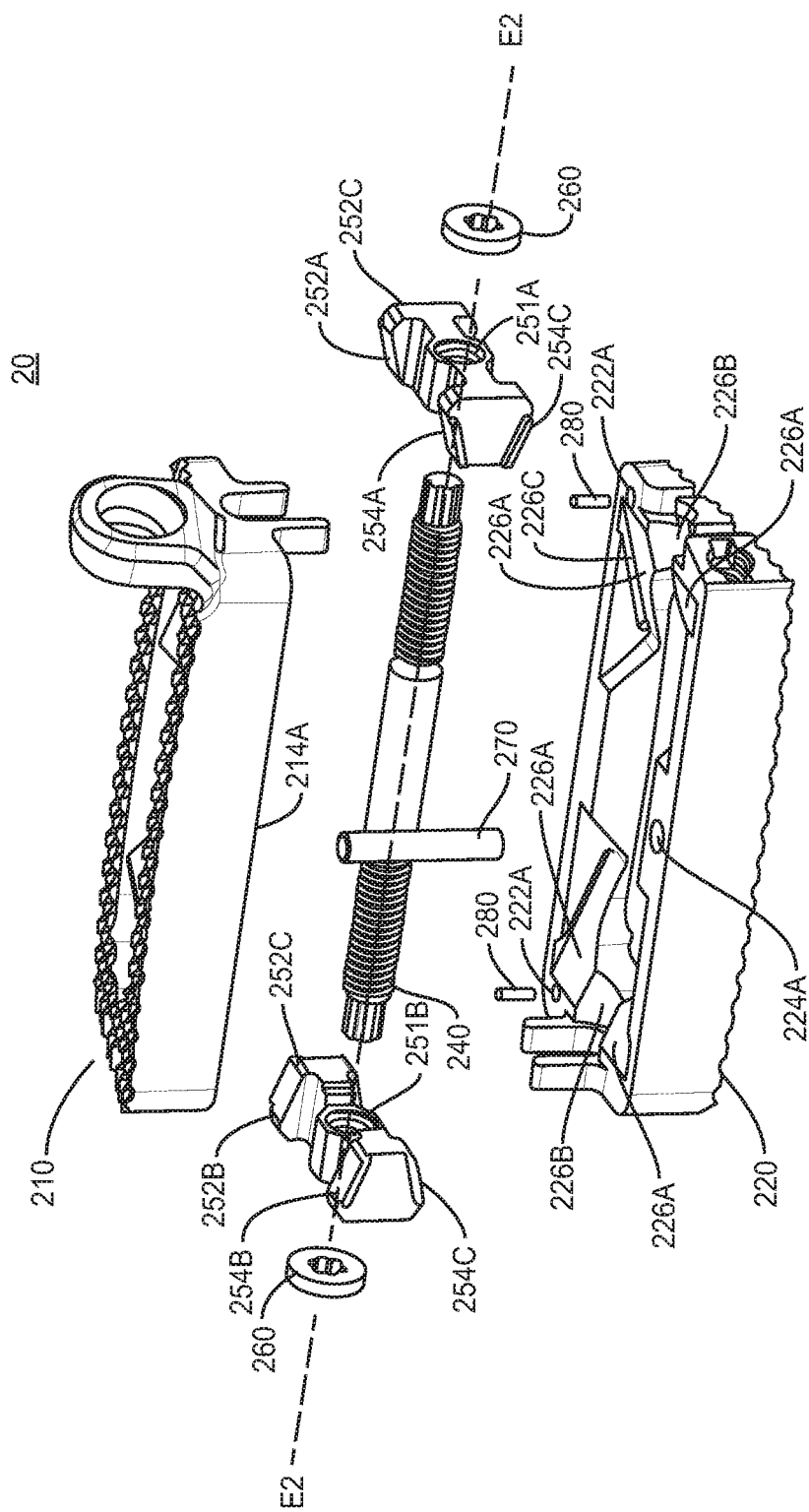
FIG. 13 is an exploded first end perspective view of one embodiment of an expandable spinal implant in accordance with the principles of the present disclosure.
Figure 14:
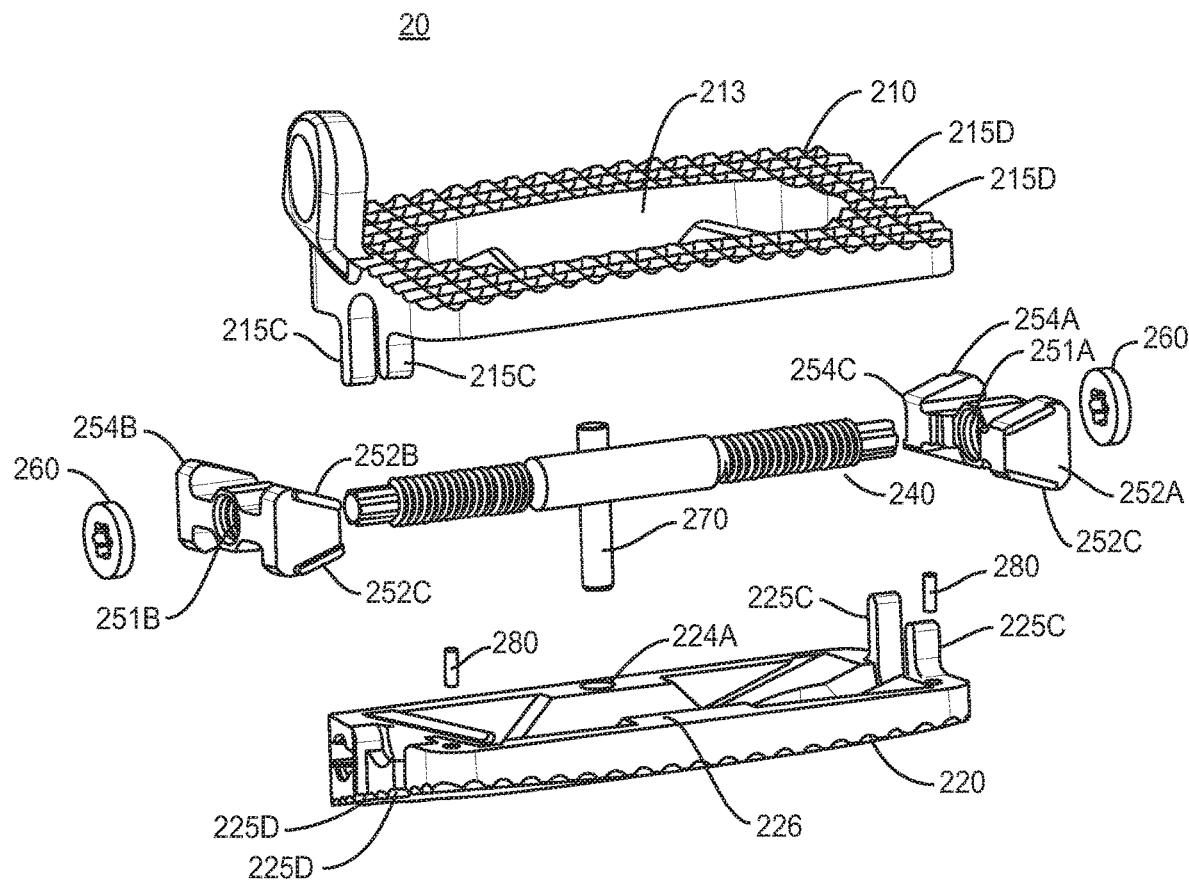
FIG. 14 is an exploded second end perspective view of one embodiment of an expandable spinal implant in accordance with the principles of the present disclosure.
Figure 15A:
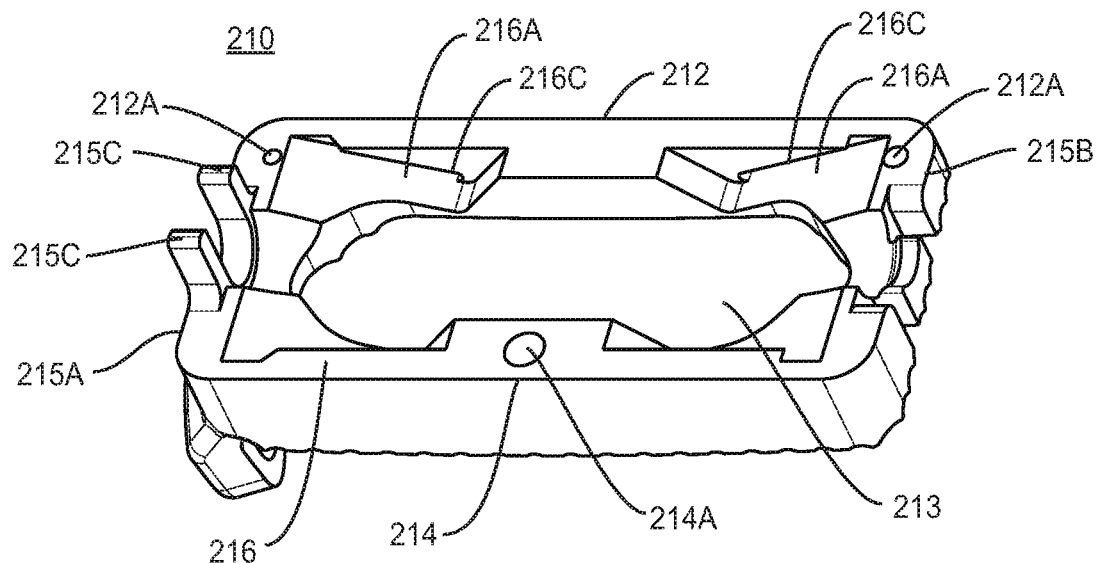
FIG. 15A is a perspective view.
Figure 15B:
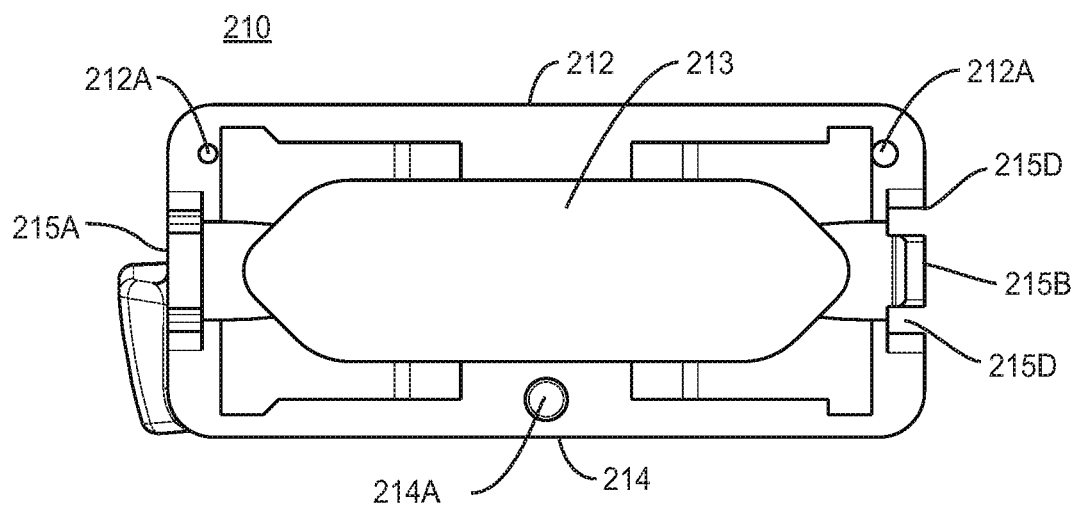
FIG. 15B is a top view, of an endplate in accordance with the principles of the present disclosure.
Figure 16:
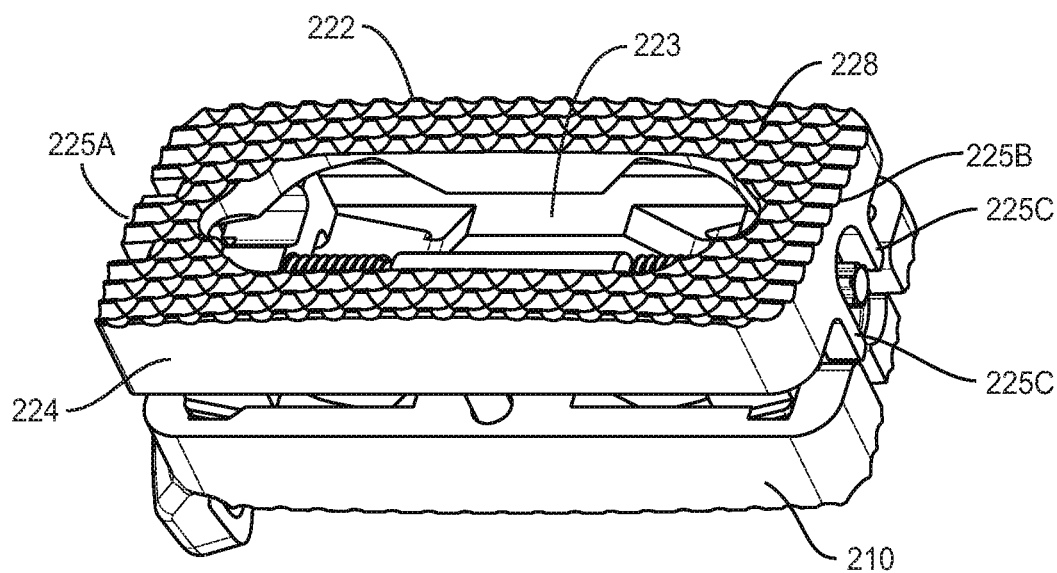
FIG. 16 is a perspective view of one embodiment of an expandable spinal implant in accordance with the principles of the present disclosure.
Figure 17A:
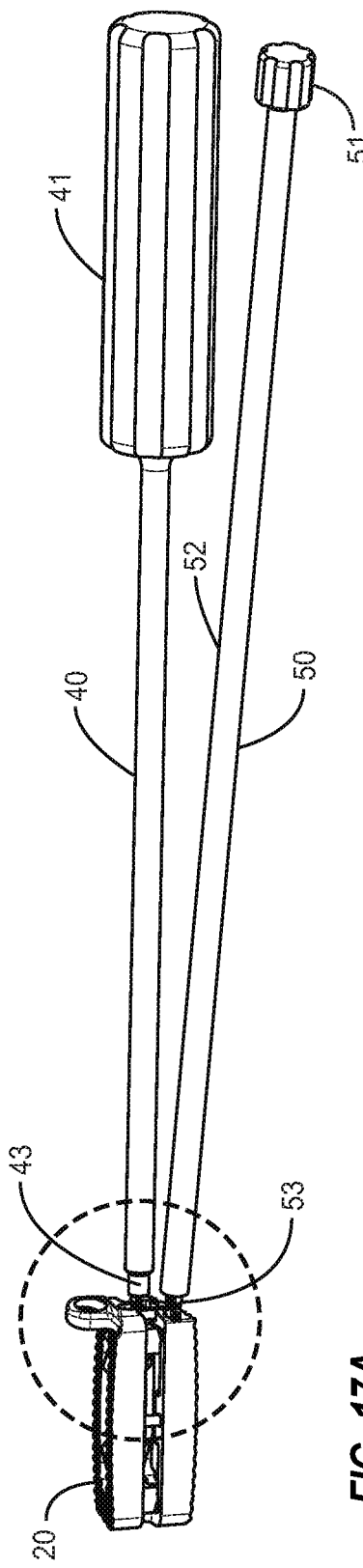
FIG. 17A is a perspective view, and FIG. 17B a close-up view, of one embodiment of an expandable spinal implant system in accordance with the principles of the present disclosure.
Figure 17B:
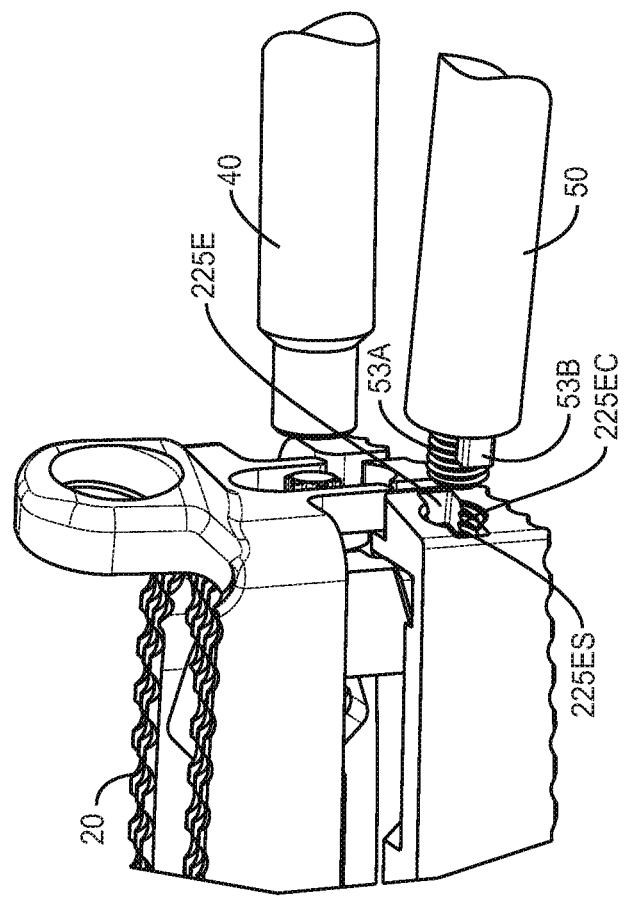
Figure 18:
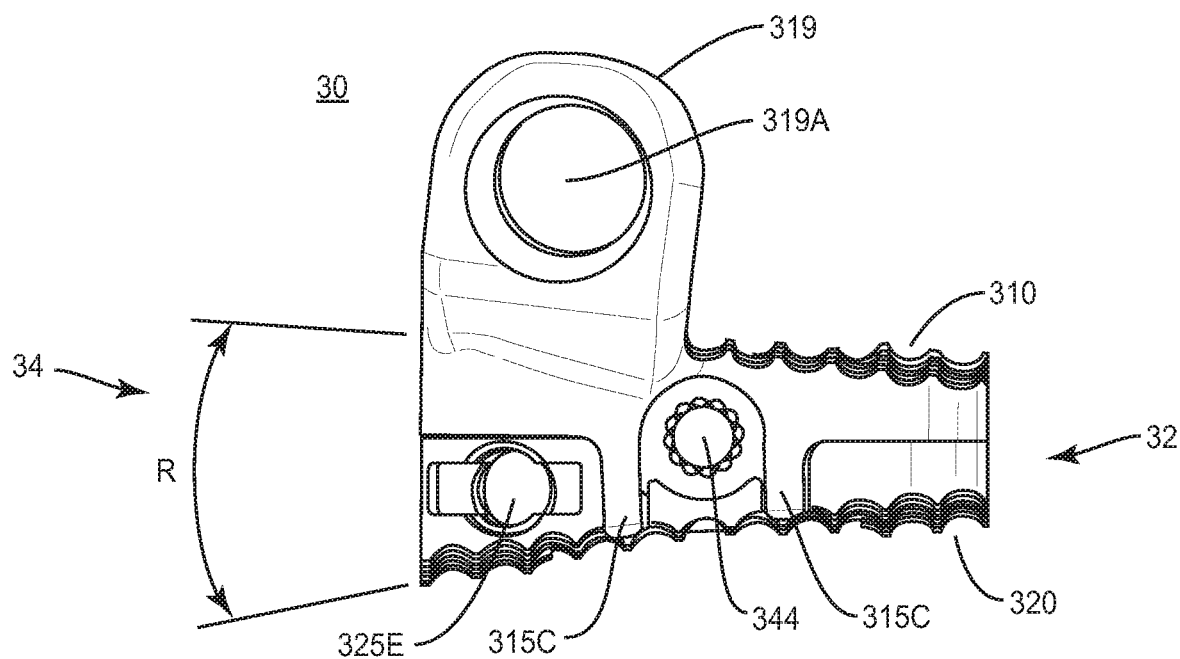
FIG. 18 is a side end view of one embodiment of an expandable spinal implant in a closed configuration in accordance with the principles of the present disclosure.
Figure 19:
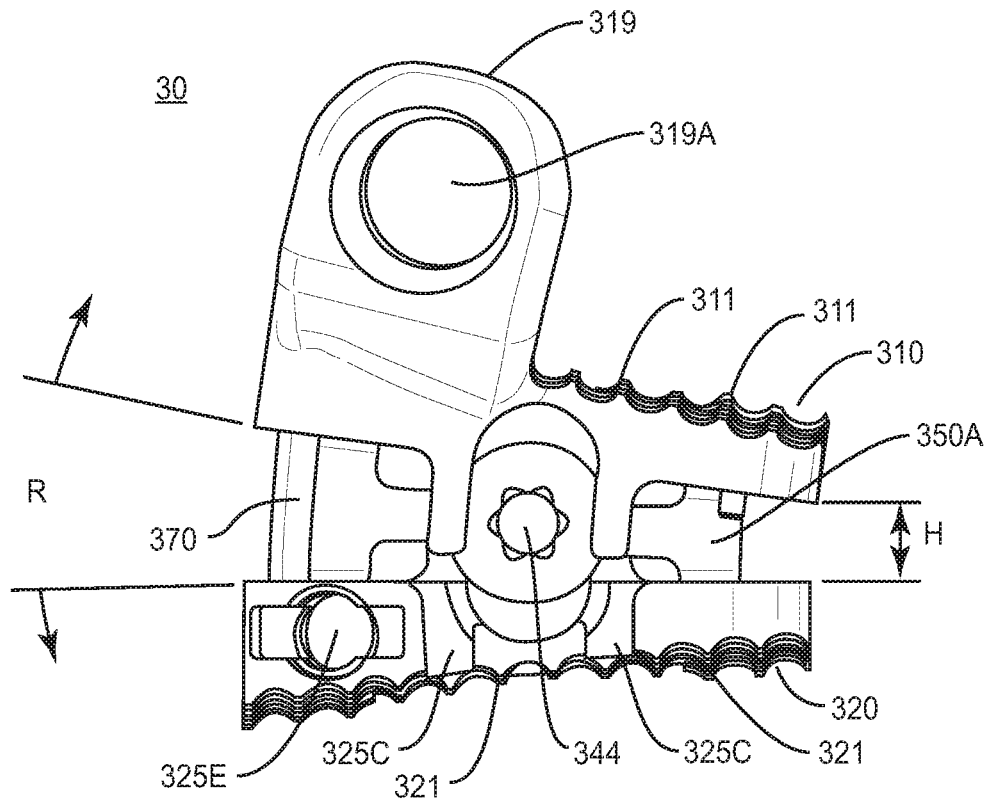
FIG. 19 is a side end view of one embodiment of an expandable spinal implant in an open configuration in accordance with the principles of the present disclosure.
Figure 20:
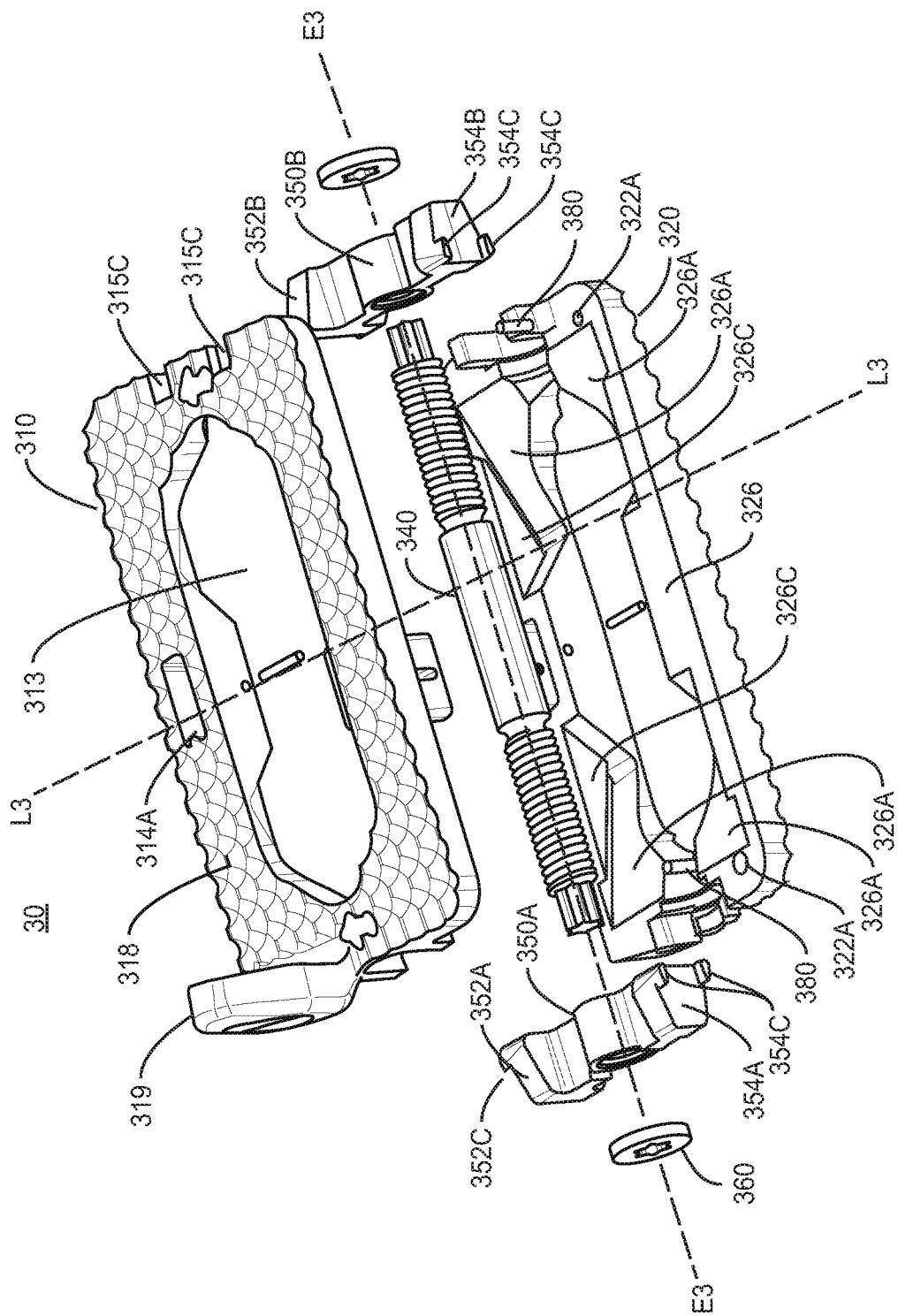
FIG. 20 is an exploded first perspective view of one embodiment of an expandable spinal implant in accordance with the principles of the present disclosure.
Figure 21:
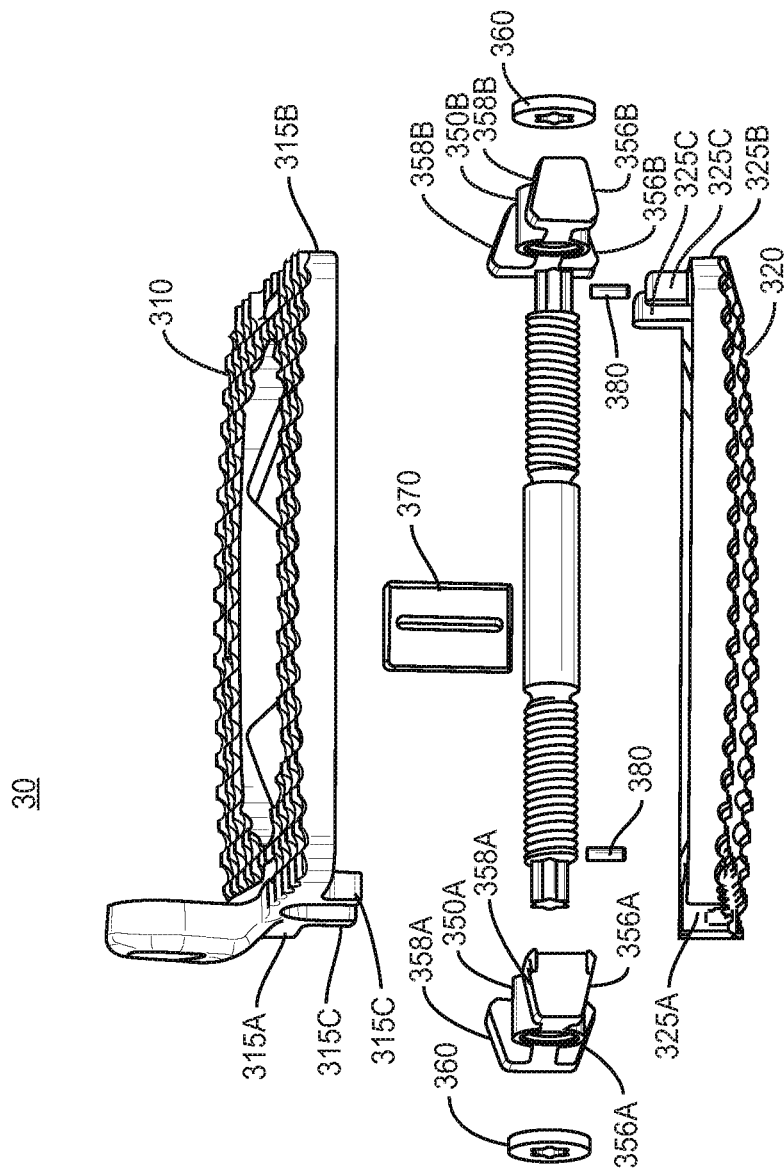
FIG. 21 is an exploded second end view of one embodiment of an expandable spinal implant in accordance with the principles of the present disclosure.
Figure 22A:
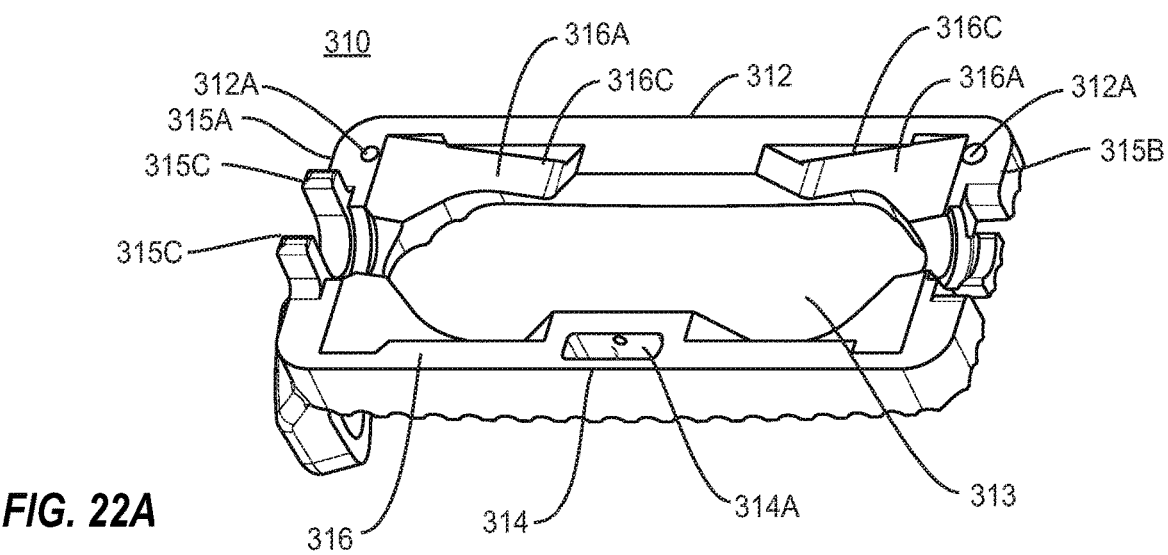
FIG. 22A is a perspective view.
Figure 22B:
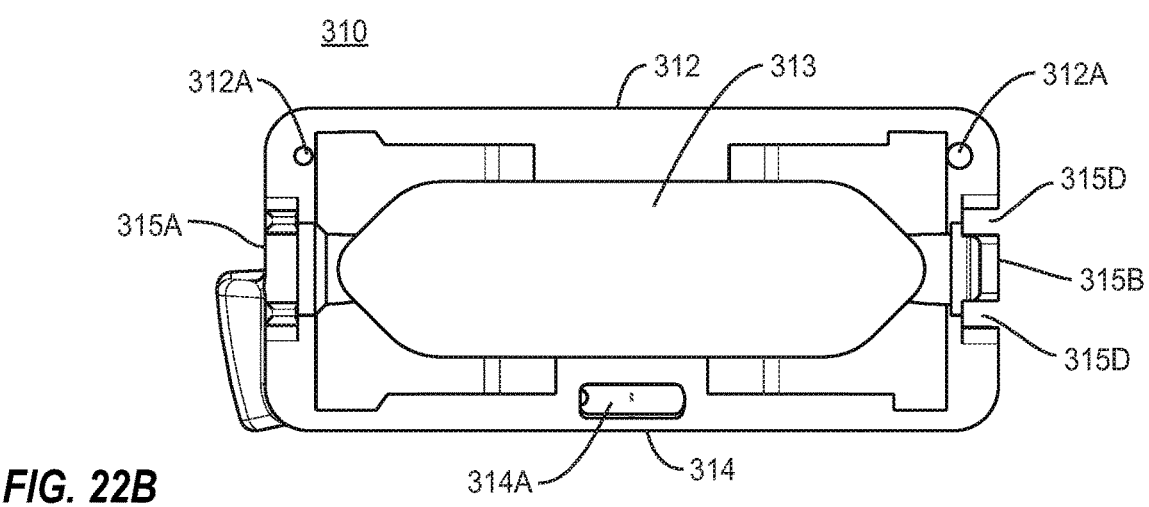
FIG. 22B is a top view, of an endplate in accordance with the principles of the present disclosure.
Figure 23:
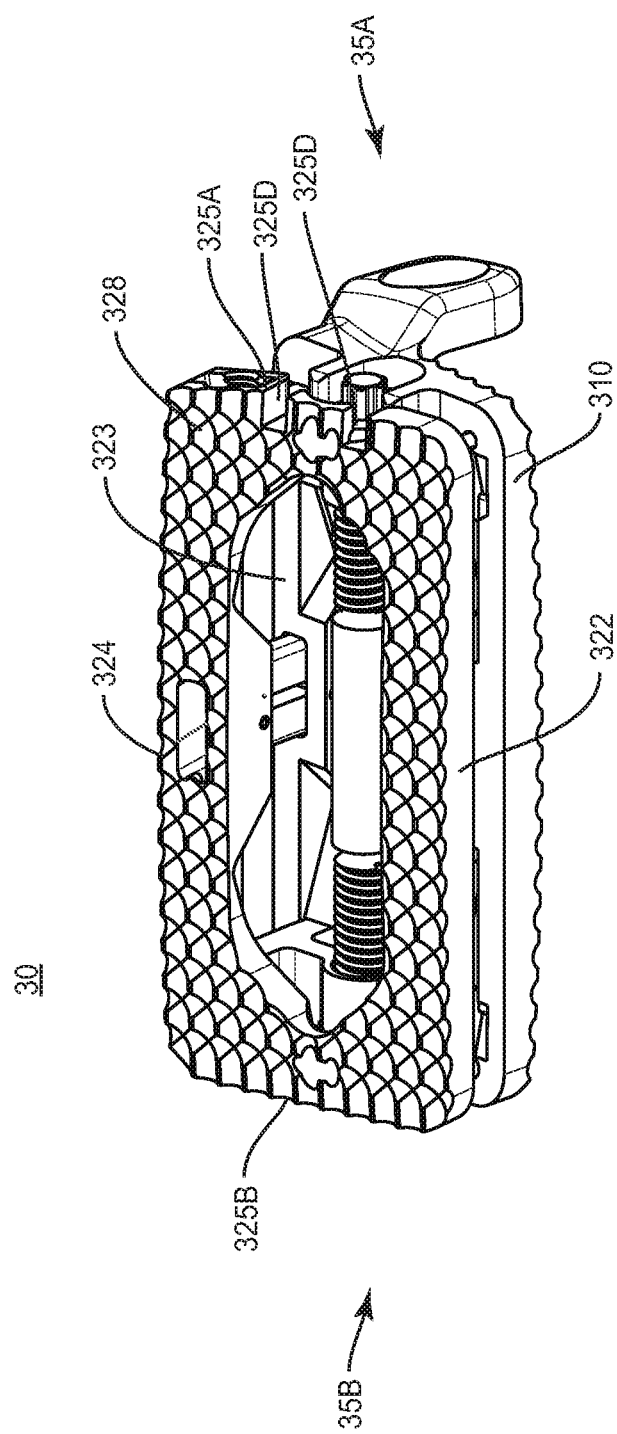
FIG. 23 is a perspective view of one embodiment of an expandable spinal implant in accordance with the principles of the present disclosure.

As depicted in FIGS. 13-15, inner surfaces 216, 226 of endplates 210, 220 may comprise corresponding ramps 216A, 226A with channels 216C, 226C disposed therein to engage protrusions 252C on the first ends 252A, 252B and protrusions 254C on the second ends 254A, 254B extending from first and second wedges 250A, 250B. The protrusions 252C, 254C and channels 216C, 226C engage so as to secure first and second endplates 210, 220 to the expansion mechanism comprising the rod assembly 240 and wedges 250A and 250B. The interaction may also aid in making the implant 20 expansion reversible such that when the wedges 250A, 250B are moved in a first direction, the lateral protrusions 252C, 254C are moved in a first direction in the lateral channels 216C, 226C to expand the first endplate 210 and the second endplate 220 away from each other. When the wedges 250A, 250B are moved in a second direction, the lateral protrusions 252C, 254C are moved in a second direction in the lateral channels 216C, 226C to contract the first endplate 210 and second endplate 220 towards each other. This reversible feature, combined with the threaded interaction between rod assembly 240 and wedges 250A, 250B renders the implant 20 capable of being incrementally expanded or contracted through a substantially infinite adjustable range of motion (bounded only by the length of the channels 216C, 226C). The design of the expansion mechanism, including the length and orientation of the channels 216C, 226C, may be adjusted to determine the expansion of implant 20. In some embodiments, the angles of the first end 252A and second end 254A of first wedge 250A and first end 252B and second end 252B of wedges 250B and corresponding ramps 216A, 226A are equal such that the endplates 210, 220 expand away from each other in parallel, with the lordotic angle of implant 20 remaining constant. In other embodiments, these various interacting wedges and ramps may comprise different angles to, e.g., provide differing amounts of expansion of the first ends 212, 222 and second ends 214, 224 of first and second endplates 210, 220 and/or different amounts of lateral expansion (see, e.g., implant 30, below). In another embodiment, implant 20, may provide an coronal expansion whereby a lateral end expands at a different rate from the opposing lateral end. In some embodiments, this may be accomplished by making the angles of wedge 250A different from those of wedge 250B, whereby lateral end 25A of implant 20 expands at a faster or slower rate than opposing lateral end 25B of implant 20, thereby introducing a coronal angle to the device.

Implant 20 may further comprise pins 280 in apertures 212a, 222a to prevent wedges 250A, 250B from translating too far in a lateral direction. In some embodiments, various designs may be used to optimize the interaction of the first and second wedges 250A, 250B with the first and second endplates 210, 220. Such configurations may include, but are not limited to: sequential ramps or tapered surfaces with varying angles; shallow angle sequential ramps or tapered surfaces leading into higher angle sequential ramps or tapered surfaces, as well as other opening mechanisms (such as the lateral post and channel system described as described in, e.g., the 952 application, incorporated herein by reference in its entirety).

In some embodiments, implant 20 may further comprise additional elements to secure the components of implant 20. In the depicted embodiment, lateral end 215A of first endplate 210 may comprise protrusions 215C configured to engage corresponding channels 225D in lateral end 225A of second endplate 220 and lateral end 225B of second endplate 220 may comprise protrusions 225C configured to engage corresponding channels 215D in lateral side 215B of first endplate 210. These components prevent displacement of first endplate 210 relative to second endplate 220 during implantation and expansion of implant 20. To prevent lateral displacement of first endplate 210 relative to second endplate 220, implant 20 comprises a rod 270 disposed within apertures 214A, 224A in first and second endplates 210, 220.

In some embodiments, implant 20 may be secured through various mechanisms to the adjacent vertebral bodies. In some embodiments, the first or second endplates 210, 220 may comprise a tab or separable plate through which a screw may be disposed. In the depicted embodiment, first endplate 210 may comprise a tab 219 comprising an aperture 219A through which a screw (not shown) may be disposed to secure endplate 210 within an intervertebral space. In some embodiments, tab 219 may not be present on implant 20, or one or more additional tabs may be present on first and/or second endplates 210, 220. Contemplated screws may comprise a threaded outer surface that engage with the inner surface of aperture 219A, which may also be threaded. The engagement between the threaded outer surface of the screw and inner surface of aperture 219A may be via pitch lock, major/minor lock, or any other thread/pitch interface. In other embodiments, implant 20 may be secured through intrinsic screws placed through apertures between inner surface 216, 226 and outer surfaces 218, 228 of endplates 210 or 220 or separable plates that may cover and/or be attached to a portion of the intervertebral implant. One or more of these screws (individually or simultaneously) may be retained by various anti-backout mechanisms such as pins, springs, movable plates or similar mechanisms to push against a portion of the screw and/or cover a portion of the screw hole after insertion of the screw. In other embodiments, implant 20 may comprise an engagement component that may be retracted within the device to allow for easy insertion into the disc space when implant 20 is in a closed or unexpanded state and which protrude from the outer surfaces 218, 228 of first and/or second endplates 210, 220 during expansion to engage the vertebral endplate(s) to prevent or decrease potential migration or expulsion of the device. Exemplary engagement mechanisms are described in, e.g., the 952 application, incorporated herein by reference in its entirety.

In some embodiments, lateral end 225A of second endplate 220 of implant 20 comprises inserter aperture 225E to engage with an insertion instrument 50 to form an expandable spinal implant system. Insertion instrument 50 comprises a handle 51, an insertion shaft 52, and an implant-engaging end 53. In some embodiments, the implant-engaging end 53 comprises a threaded portion 53A and side protrusions 53B. In the depicted embodiment, inserter aperture 225E comprises a threaded central portion 225EC designed to engage threaded portion 53A of insertion instrument 50 and side slots 225ES designed to engage side protrusions 53B of insertion instrument 50. In some embodiments, the angle of inserter aperture 225E may be adjusted to allow insertion instrument 50 to be attached to implant 20 in multiple orientations. This provides user flexibility to place implant 20 within intervertebral space with first endplate 210 superior to second endplate 220 or with first endplate 210 inferior to second endplate 220 such the tab may be used to secure implant 20 in either the cephalad or caudad vertebral bodies.

FIGS. 18-24 show various configurations of an implant 30 embodiment according to the present disclosure. Implant 30 has a first end 32 and a second end 34 and lateral sides 35A and 35B therebetween and is generally similar in construction to implant 20 above and comprises a first endplate 310 and second endplate 320 operably engaged to an expansion mechanism comprising a rod assembly 340 and first and second wedges 350A, 350B disposed therebetween. First endplate 310 includes a first end 312, a second end 314, a first side surface 315A and an opposing second side surface 315B, an inner surface 316, and an outer surface 318.

Second endplate 320 includes a first end 322, a second end 324, a first side surface 325A and an opposing second side surface 325B, an inner surface 326, and an outer surface 328. In one embodiment, the endplates 310, 320 includes projections 311, 321 configured to engage a surface of the endplate of the adjacent vertebral body (not shown). Projections 311, 321 may comprise various anti-migration, anti-expulsion, and/or osseointegration features including, but not limited to: ridges, teeth, pores, and coatings (including but not limited to porous titanium coatings such as those provided on Capstone PTC™ implants available from Medtronic). The endplates 310, 320 may further comprise at least one opening 313, 323 defined therein, configured to allow bone growth materials to be packed, placed, or loaded into the implant 30. Similar to implant 20, first ends of first endplate 210 and second endplate 220 are not operably engaged such that both first and second ends of first endplate 210 may expand away from second endplate 220. In some embodiments, the first and second ends of first endplate 210 expand at different rates such that the lordotic angle (e.g., zero degrees to 45 degrees) of the implant 20 changes while the height H of the device increases. In this manner, implant 30 provides a dual expansion along two dimensions.

Figure 24:
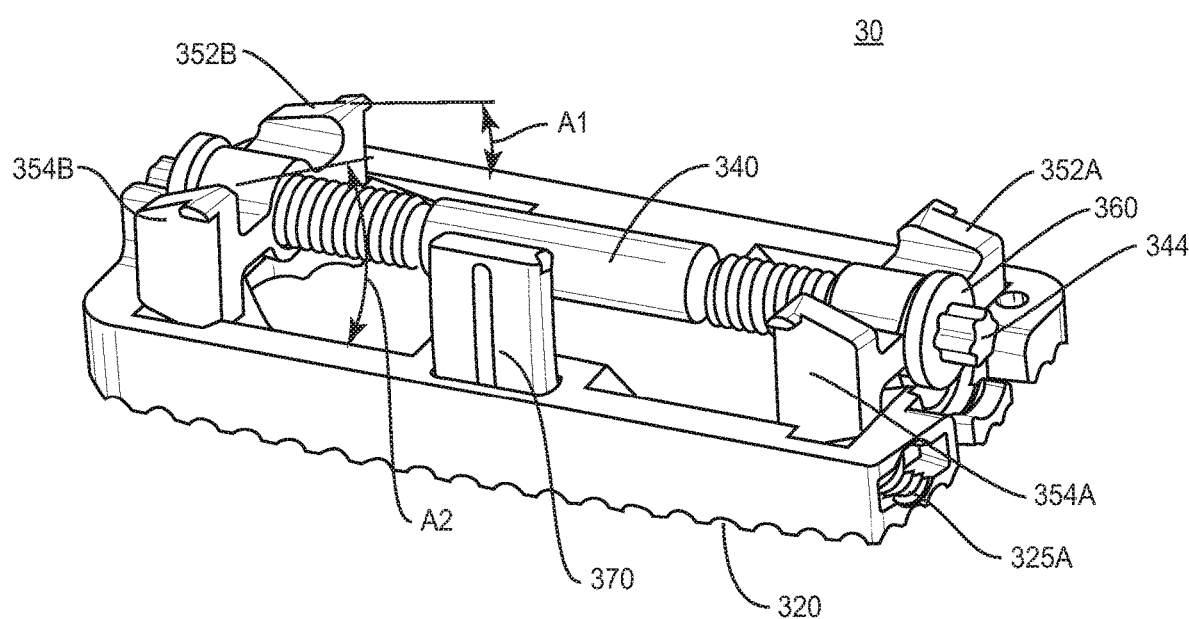
FIG. 24 is a perspective view of a second endplate and expansion mechanism of one embodiment of an expandable spinal implant in accordance with the principles of the present disclosure.
Figure 25:
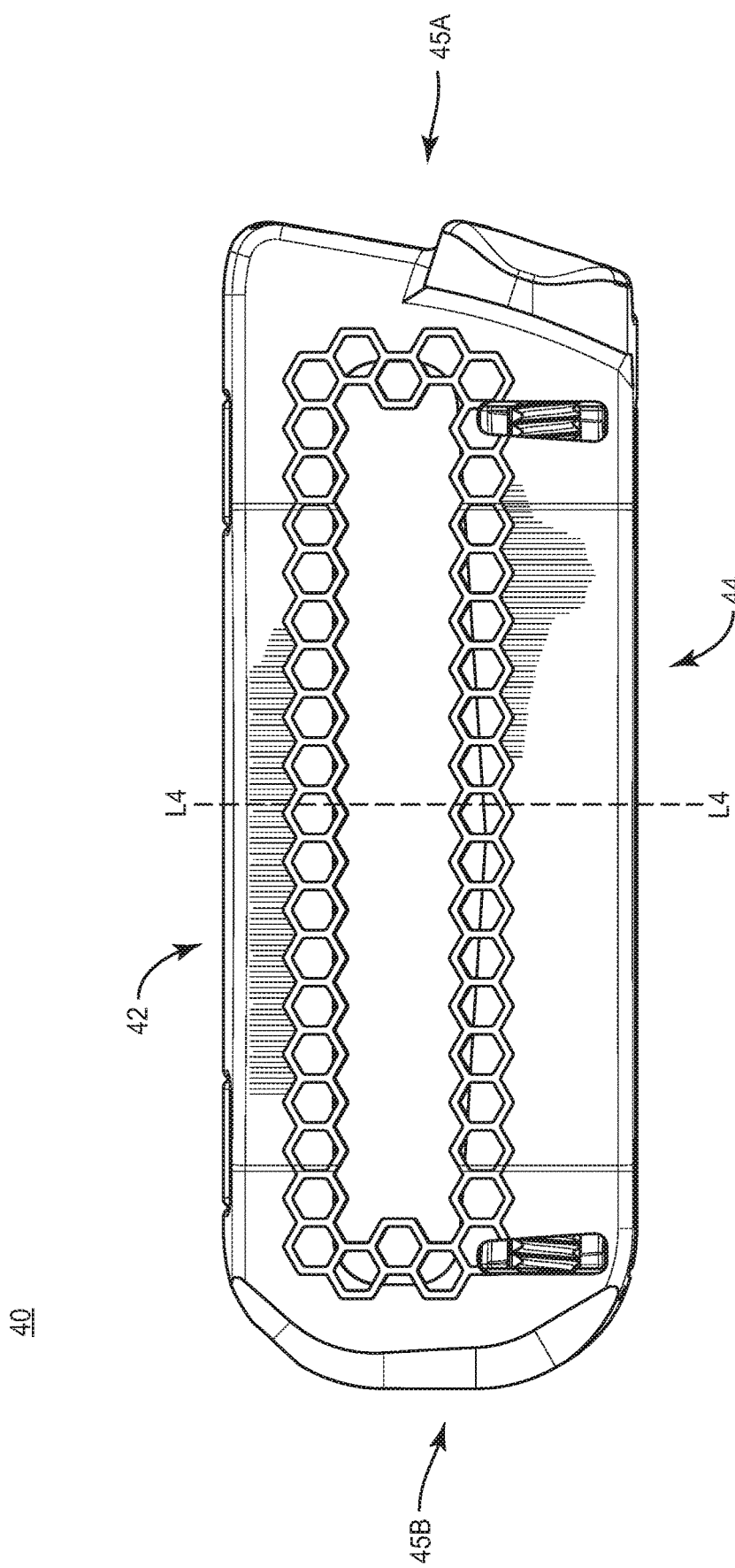
FIG. 25 is a top view of one embodiment of an expandable spinal implant in accordance with the principles of the present disclosure.
Figure 26:
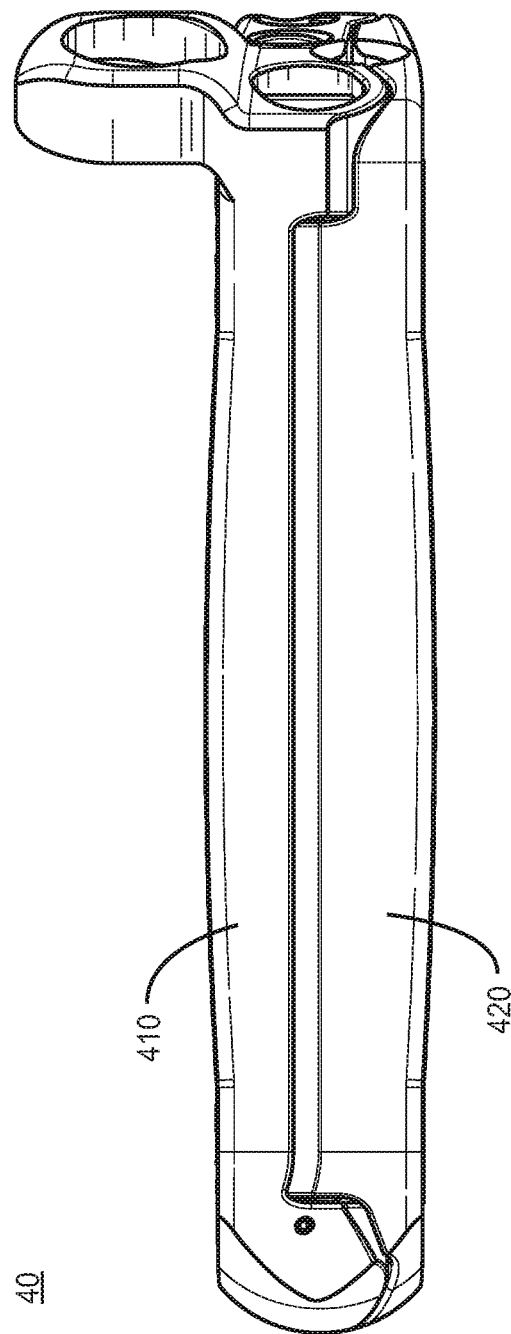
FIG. 26 is an end view of one embodiment of a closed expandable spinal implant in accordance with the principles of the present disclosure.
Figure 27:
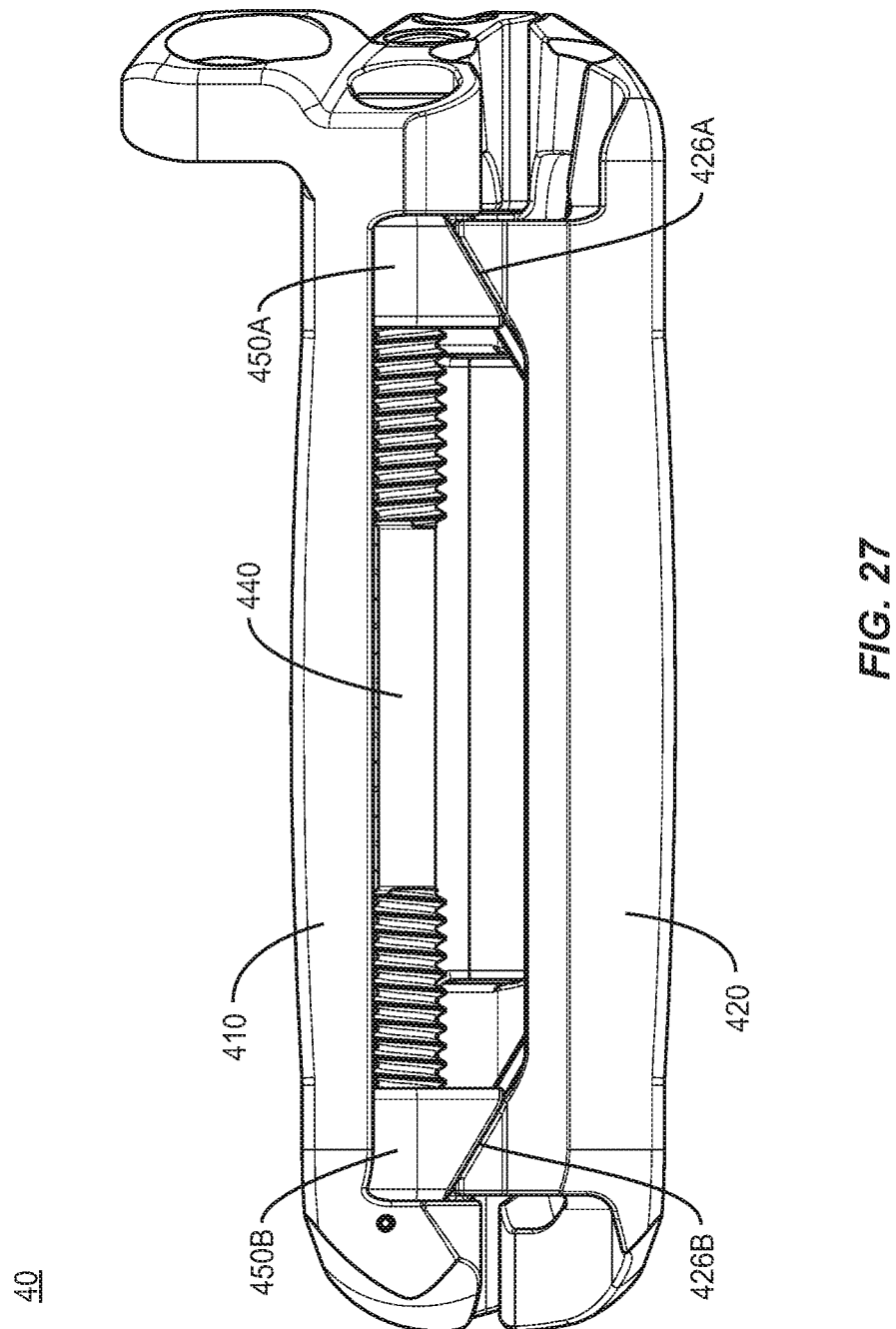
FIG. 27 is an end view of one embodiment of an open expandable spinal implant in accordance with the principles of the present disclosure.
Figure 28:
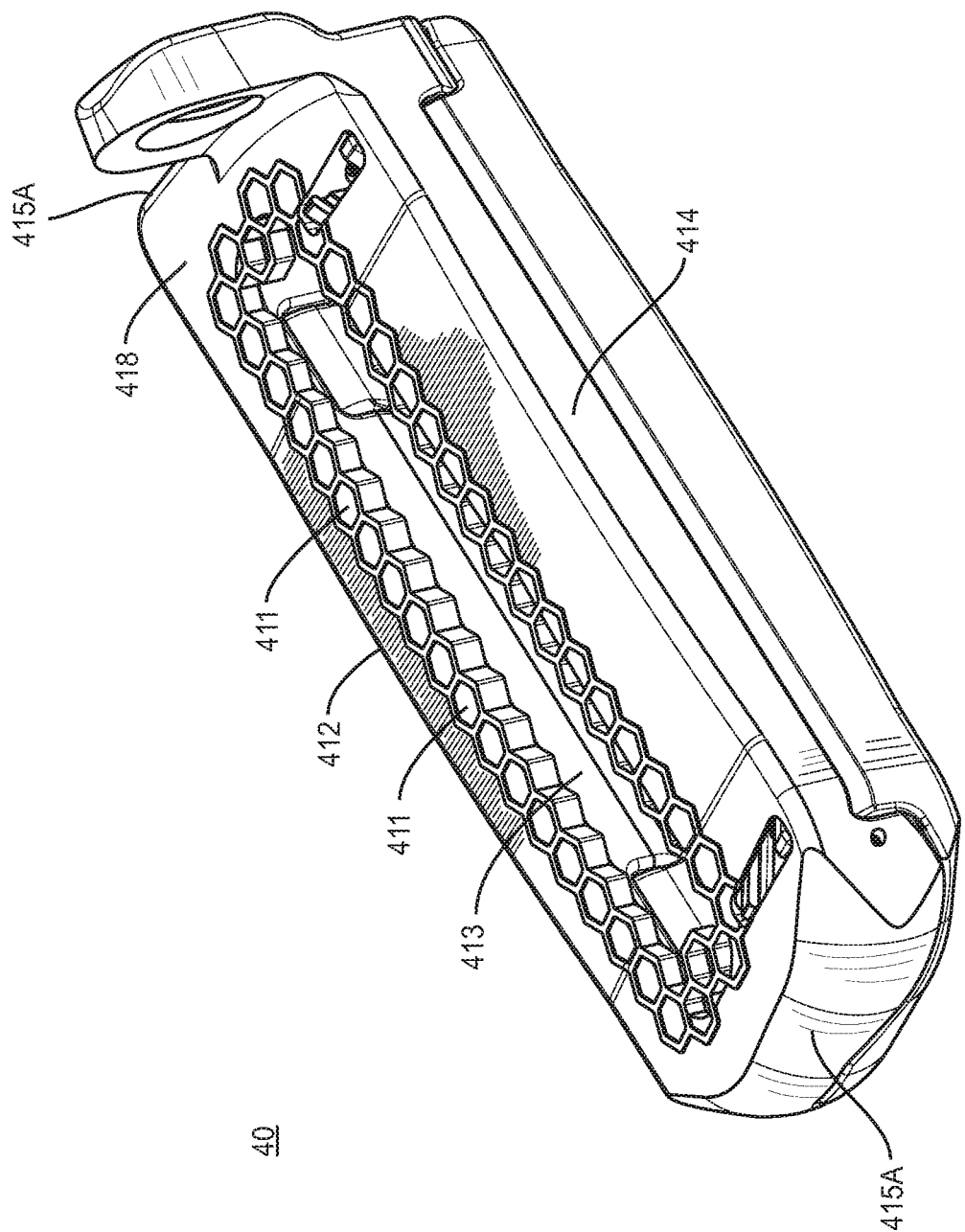
FIG. 28 is a perspective view of one embodiment of a closed expandable spinal implant in accordance with the principles of the present disclosure.
Figure 30:
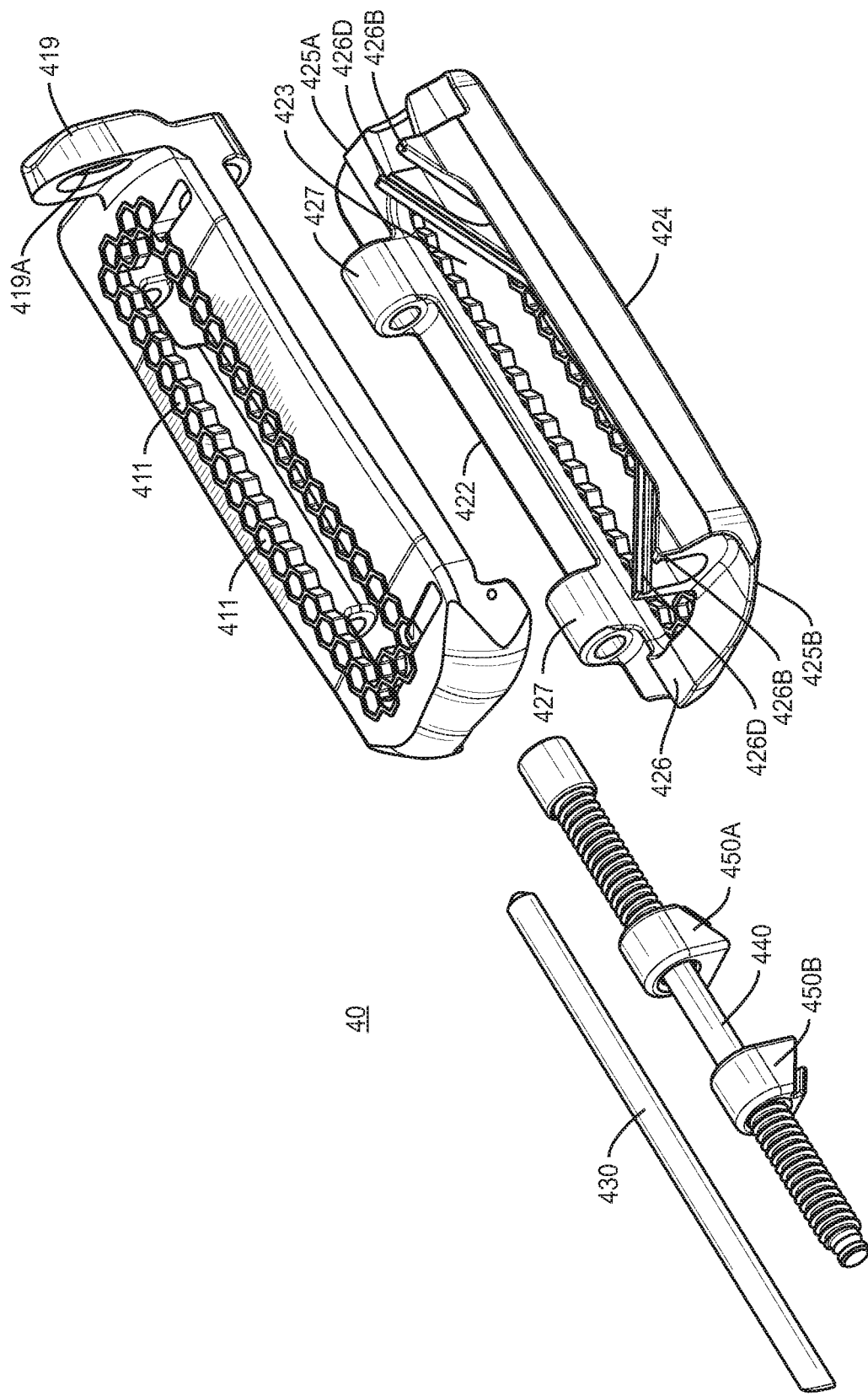
FIG. 30 is an exploded top perspective view of one embodiment of an expandable spinal implant in accordance with the principles of the present disclosure.
Figure 33:
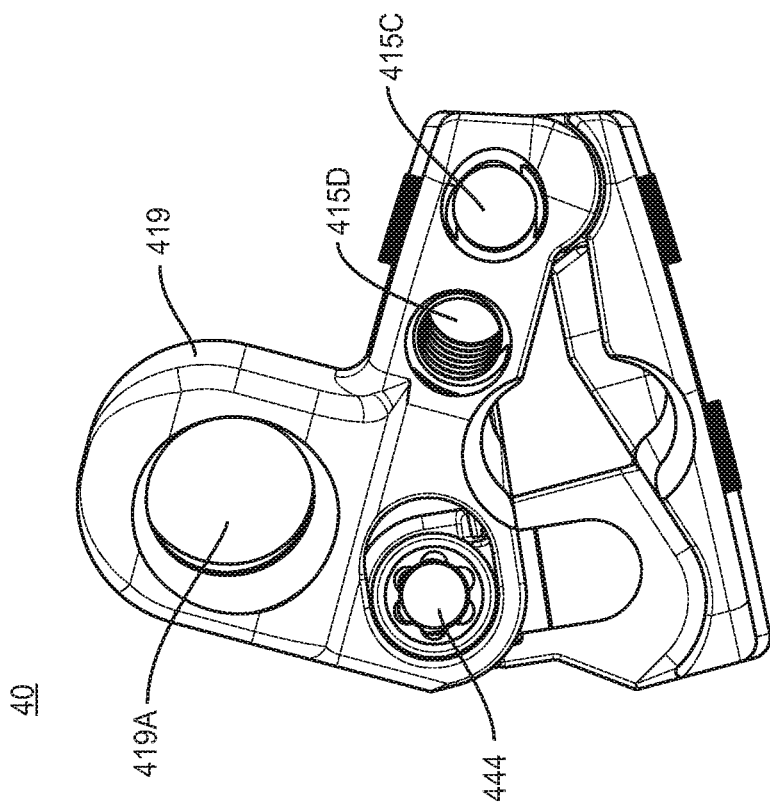
FIG. 33 is a side view of one embodiment of an open expandable spinal implant in accordance with the principles of the present disclosure.
Figure 32:
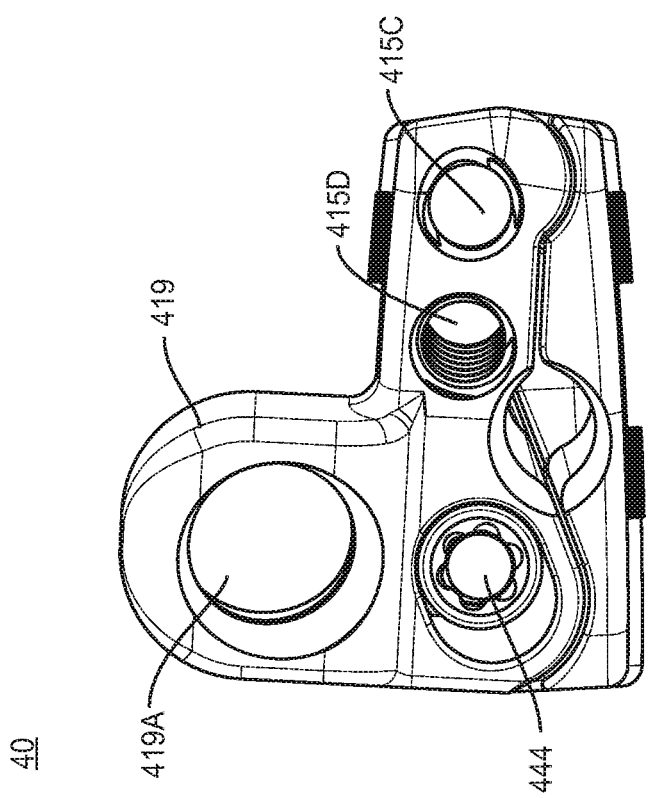
FIG. 32 is a side view of one embodiment of a closed expandable spinal implant in accordance with the principles of the present disclosure.

Like as described above for implant 20, implant 30 may comprise an expansion mechanism comprised of rod assembly 340 having a longitudinal axis E3-E3 and wedges 350A and B designed to expand first endplate 310 and second endplate 320 away from each other as wedges 350A, 350B are translated along rod assembly 340. First wedge 350A may comprise a first end 352A and a second end 354A. Similarly, second wedge 350B may comprise a first end 352B and a second end 354B. In some embodiments, the upper and/or lower surfaces of wedge first ends 352A, 352B and second ends 354A, 354B may be ramped or wedge-shaped and suitable for urging a complementary ramped or contoured surface on the inside of endplates 310, 320 so as to gradually move the endplates 310, 320 away from each other as the wedges 350A, 350B are advanced along the rod assembly 340. In some embodiments, first and second wedges 350A, 350B may be positioned medially when implant 30 is in a closed state and travel laterally towards the sides to expand implant 30. In other embodiments, first and second wedges 350A, 350B may be positioned laterally when implant 30 is in a closed state and travel medial towards mid-longitudinal axis L3-L3 to expand implant 30. As depicted in FIG. 24, the angle A1 of the first ends 352A, 352B of wedges 350A, 350B are different from the angle A2 of the second ends 354A, 354B to provide different rates of expansion along the first and second ends of the device. These differing angles result in both a lordotic expansion and a height increase as implant 30 is expanded. In another embodiment, implant 30, may provide an coronal expansion whereby a lateral end expands at a different rate from the opposing lateral end. This may be accomplished by, e.g., having the angles of first or second ends 352A, 354A of wedge 350A may be different from the angles of first or second ends 352B, 354B of wedge 350B.

Implant 30 incorporates additional features to facilitate the differing rate of expansion along the first and second ends of implant 30. For example, in some embodiments, the upper 358A, 358B and/or lower 356A, 356B surfaces of first and second wedges 350A, 350B may be curved so as to accommodate the change in relative angle between inner surfaces 316, 326 and upper 358A, 358B and lower 356A, 356B surfaces of first and second wedges 350A, 350B that occurs as implant 30 is expanded or contracted. Similarly, to ensure that the protrusions 352C and protrusions 354C are secure within channels 316c, 326c throughout the range of expansion, the width of the channels 316c, 326c may gradually increase across the lateral length of the channels so as to be widest at the side occupied by the wedge when the device is in its most expanded state. That is, the width of channels 316c, 326C may widen in order to accommodate the change in angle between protrusions 352C and protrusions 354C relative to channels 316C, 326C as the device is expanded. In other embodiments, the channels 316C, 326C are a constant width and wide enough to accommodate protrusions 352C, 354C across their entire length. However, such constant width channels would result in a loose and less secure channel-protrusion fit when implant 30 is collapsed or only partially expanded.

Implant 30 may further comprise pins 380 in apertures 312a, 322a to prevent wedges 350A, 350B from translating too far in a lateral direction. In some embodiments, various designs may be used to optimize the interaction of the first and second wedges 350A, 350B with the first and second endplates 310, 320. Such configurations may include, but are not limited to: sequential ramps or tapered surfaces with varying angles; shallow angle sequential ramps or tapered surfaces leading into higher angle sequential ramps or tapered surfaces, as well as other opening mechanisms (such as the lateral post and channel system described as described in, e.g., the '952 application, incorporated herein by reference in its entirety).

In some embodiments, implant 30 may further comprise additional elements to secure the components of implant 30. In the depicted embodiment, lateral end 315A of first endplate 310 may comprise protrusions 315C configured to engage corresponding channels 325D in lateral end 325A of second endplate 320 and lateral end 325B of second endplate 320 may comprise protrusions 325C configured to engage corresponding channels 315D in lateral side 315B of first endplate 310. These components prevent displacement of first endplate 310 relative to second endplate 320 during implantation and expansion of implant 30. To prevent lateral displacement of first endplate 310 relative to second endplate 320, implant 30 comprises a rod 370 disposed within apertures 314A, 324A in first and second endplates 310, 320. In some embodiments, rod 370 may be curved to accommodate the lordotic expansion.

In some embodiments, coronal adjustment may be accomplished by making the angles of wedge 350A different from those of wedge 350B, whereby lateral end 35A of implant 30 expands at a faster or slower rate than opposing lateral end 35B of implant 30, thereby introducing a coronal angle to the device in addition to the lordotic and height expansion. By individually altering the angles of the first end 352A of first wedge 350A, first end 352B of second wedge 350B, second end 354A of first wedge 350A, and second end 354B of second wedge 350B, any desired relative positioning can be obtained between the planes of the first and second endplates 310, 320. It is understood that various aspects of the device, such as the curvature of the upper and lower surfaces of wedges 350A, 350B, the width of channels 316C, 326C, and curvature and positioning of rod 370 may be adjusted so as to accommodate the desired relative positioning to be obtained between the first and second endplates 310, 320 when implant 30 is expanded.

In some embodiments, implant 30 may be secured through various mechanisms to the adjacent vertebral bodies. In some embodiments, the first or second endplates 310, 320 may comprise a tab or separable plate through which a screw may be disposed. In the depicted embodiment, first endplate 310 may comprise a tab 319 comprising an aperture 319A through which a screw (not shown) may be disposed to secure endplate 310 within an intervertebral space. In some embodiments, tab 319 may not be present on implant 30, or one or more additional tabs may be present on first and/or second endplates 310, 320. Contemplated screws may comprise a threaded outer surface that engages with the inner surface of aperture 319A, which may also be threaded. The engagement between the threaded screw outer surface and the inner surface of aperture 319A may be via pitch lock, major/minor lock, or any other thread/pitch interface. In other embodiments, implant 30 may be secured through intrinsic screws placed through apertures between inner surfaces 316, 326 and outer surfaces 318, 328 of endplates 310 or 320 or separable plates that may cover and/or be attached to a portion of the intervertebral implant. One or more of these screws (individually or simultaneously) may be retained by various anti-backout mechanisms such as pins, springs, movable plates or similar mechanisms to push against a portion of the screw and/or cover a portion of the screw hole after insertion of the screw. In other embodiments, implant 30 may comprise one or more engagement components that may be retracted within the device to allow for easy insertion into the disc space when implant 30 is in a closed or unexpanded state, and which may protrude from the outer surfaces 318, 328 of first and/or second endplates 310, 320 during expansion to engage the vertebral endplate(s) to prevent or decrease potential migration or expulsion of the device from the intervertebral space. Exemplary engagement mechanisms are described in, e.g., the 952 application, incorporated herein by reference in its entirety.

As described above for implant 20, one or both ends of rod assembly 340 may comprise an interface 344 configured to be operably engaged by a driver instrument (not shown) to rotate the rod assembly 340. The driver instrument may be generally similar to driver instrument 40, discussed above. The rod interface 244 may comprise a drive receptacle configured to cooperate with implant engaging end of the driver instrument. The drive connection between the driver instrument and the rod interface 244 may comprise a variety of drive interfaces including but not limited to: multi-lobular drives; hexalobular drives; cross or Phillips head drives; straight or "flat head" drives; square or other polygonal drives; and/or combinations thereof.

In some embodiments, lateral end 325A of second endplate 320 of implant 30 comprises inserter aperture 325E to engage with an insertion instrument (not shown) to form an expandable spinal implant system. The inserter aperture 325E and insertion instrument may be generally similar to inserter aperture 225E and insertion instrument 50, discussed above. In some embodiments, the angle of inserter aperture 325E may be adjusted to allow the insertion instrument to be attached to implant 30 in multiple orientations. This provides user flexibility to place implant 30 within intervertebral space with first endplate 310 superior to second endplate 320 or with first endplate 310 inferior to second endplate 320 such the tab may be used to secure implant 30 in either the cephalad or caudad vertebral bodies.

FIGS. 25-33 show various configurations of an implant 40 embodiment according to the present disclosure. Implant 40 has a first end 42 and a second end 44 defining an axis L4-L4, a lateral side 45A and an opposing lateral side 45B and is generally similar in construction and operation to implant 10 described above, as will be readily apparent to one of ordinary skill in the art. Implant 40 may comprise a first endplate 410 and second endplate 420 operably engaged to one another via a hinge mechanism along a first end of the implant comprising hinge protrusions 417 and 427 and pin 430, and an expansion mechanism comprising a rod assembly 440 and first wedge 450A and a second wedge 450B disposed therebetween. First endplate 410 includes a first end 412, a second end 414, a first side surface 415A and an opposing second side surface 415B, an inner surface 416, and an outer surface 418. Second endplate 420 includes a first end 422, a second end 424, a first side surface 425A and an opposing second side surface 425B, an inner surface 426, and an outer surface 428. The first and second endplates are similar to endplates 110 and 120 of implant 10, and may include any features described above, including but not limited to, various anti-migration, anti-expulsion, and/or osseointegration features including, but not limited to: ridges, teeth, pores, and coatings (including but not limited to porous titanium coatings such as those provided on Capstone PTC™ implants available from Medtronic) or openings defined therein, configured to allow bone growth materials to be packed, placed, or loaded into the implant 40. In the depicted embodiment, the first and second endplates of implant 40 each comprise a large central opening 413 and 423 surrounded by a border of smaller hexagonal openings 411 and 421. These hexagonal openings may be completely filled, partially filled such that at least a portion of the interior comprises an aperture through the endplate, or completely open such that the entire portion of the interior comprises an aperture through the endplate.

Like implant 10, implant 40 is expanded by translating the first and second wedges along the rod assembly, whereby the first and second wedges interact with an endplate of implant 40 to expand or open the implant and increase the lordotic angle. In the depicted embodiment, the lower surface of the first and second wedges interacts with protrusions 426B from the inner surface of the second endplate to cause implant 40 to expand. As can be seen in, e.g., FIGS. 29 and 30, the lower surface of the first and second wedges may comprise a lipped protrusion 456AP and 456BP configured to engage with a corresponding lipped channel 426D in the protrusion from the inner surface of the second endplate. Accordingly, the lipped protrusions 456AP and 456BP of the first and second wedges may be configured to expand implant 40 when moved in a first direction in the lipped channel 426D in the protrusion from the inner surface of the second endplate, and may be configured to contract or close implant 40 when the lipped protrusions 456AP and 456BP of the first and second wedges are moved in a second direction in the lipped channel 426D in the protrusion from the inner surface of the second endplate.

In some embodiments, one or both ends of rod assembly 440 may comprise an interface 444 configured to be operably engaged by a drive shaft (not shown) to rotate the rod 440. The rod interface 444 may comprise a drive receptacle configured to cooperate with an implant-engaging end of the drive shaft. The drive connection between the driver shaft and the rod interface 444 may comprise a variety of drive interfaces including but not limited to: multi-lobular drives; hexalobular drives; cross or Phillips head drives; straight or "flat head" drives; square or other polygonal drives; and/or combinations thereof.

In some embodiments, implant 40 may be secured through various mechanisms to the adjacent vertebral bodies. In some embodiments, the first or second endplates 410, 420 may comprise a tab or separable plate through which a screw may be disposed. In the depicted embodiment, first endplate 410 may comprise a tab 419 comprising an aperture 419A through which a screw (not shown) may be disposed to secure endplate 410 within an intervertebral space. In some embodiments, tab 419 may not be present on implant

40, or one or more additional tabs may be present on first and/or second endplates 410, 420. Contemplated screws may comprise a threaded outer surface that engages with the inner surface of aperture 419A, which may also be threaded. The engagement between the threaded screw outer surface and the inner surface of aperture 419A may be via pitch lock, major/minor lock, or any other thread/pitch interface. In other embodiments, implant 40 may be secured through other means as described above, such as an intrinsic screw placed through apertures directly in endplates 410 and/or 420.

Figure 34A:
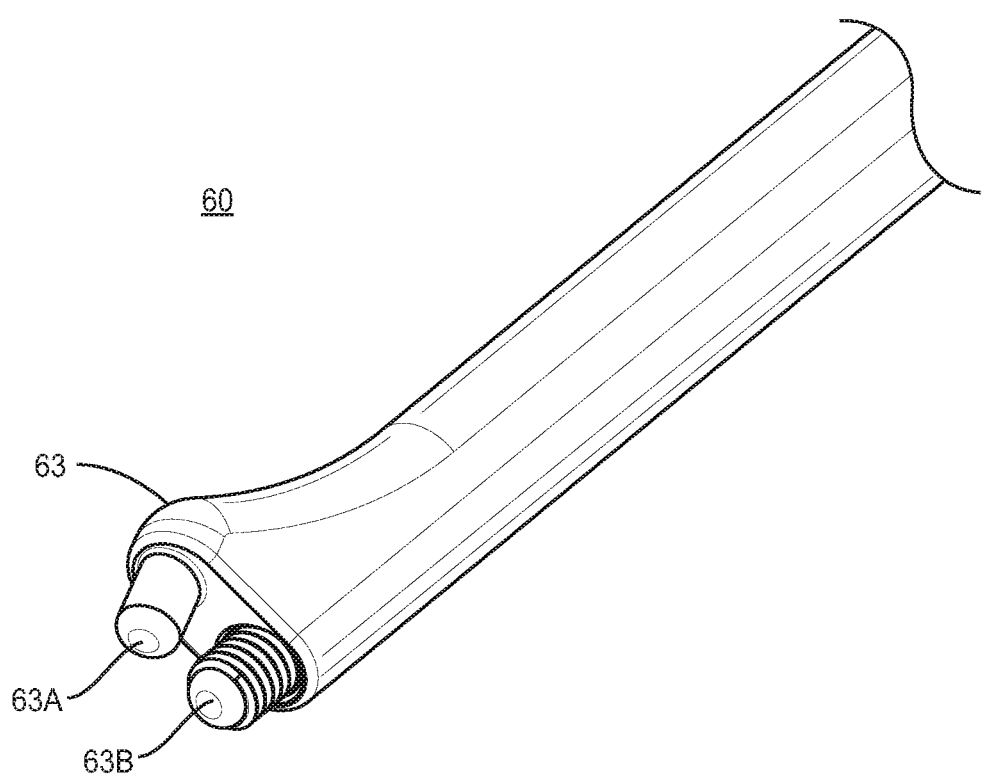
FIG. 34A is a perspective view of an insertion instrument alone and in use with one embodiment of an expandable spinal implant in a first configuration (FIG. 34B) and second configuration (FIG. 34C) in accordance with the principles of the present disclosure.
Figure 34B:
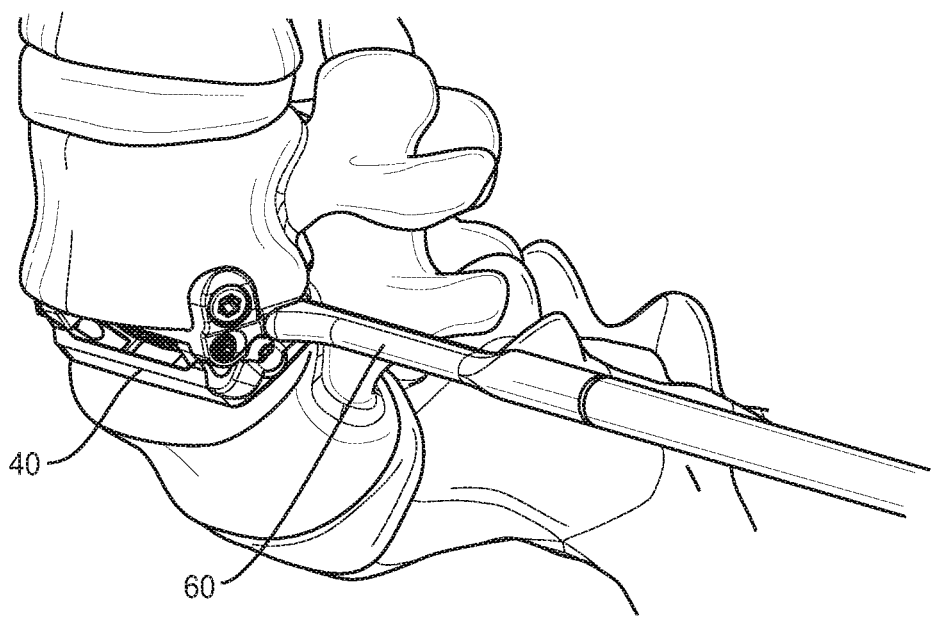
Figure 34C:
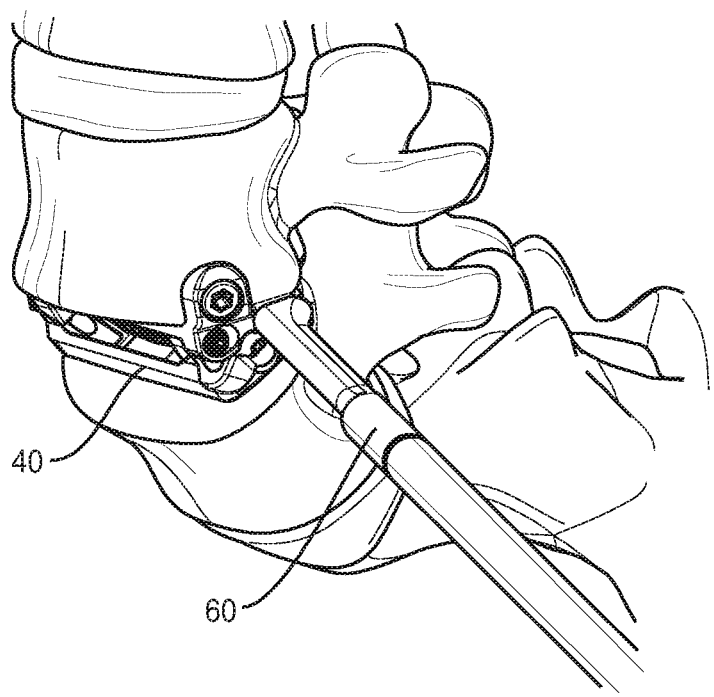

In some embodiments, lateral end 415A of first endplate 410 of implant 40 comprises attachment apertures 415C and 415D to engage with an insertion instrument 60, although similar apertures are contemplated in second endplate 420. Insertion instrument 60 may comprise a implant-engaging end 63. In some embodiments, implant engaging end 63 may comprise a first protrusion 63A and a second protrusion 63B. First protrusion and 63A and second protrusion 63B are angled relative to one another, i.e., not parallel. In the depicted embodiment, first protrusion 63A is threaded and substantially parallel to the longitudinal axis of the insertion instrument 60, and second protrusion 63B is not threaded and angled at approximately 15 degrees relative to the longitudinal axis of the insertion instrument 60. However, it should be understood that the angles of first and second protrusions 63A, 63B may be varied as desired, and that either or both may be threaded or unthreaded. Apertures 415C and 415D are configured to be engagable with either of first protrusion 63A and second protrusion 63B in a symmetrically flippable manner (i.e., aperture 415C may receive first protrusion 63A or second protrusion 63B, and aperture 415C may similarly receive either first protrusion 63A or second protrusion 63B). In this way, the insertion instrument 60 may engage implant 40 at different orientations to accommodate different angles of access as depicted in FIGS. 34B and 34C, as may be necessary based on the requirements of a particular procedure. The symmetrically flippable nature of insertion instrument 60 may also allow its use in either side of the patient. The reduced size of its engagement features of insertion instrument 60 allows it to be employed on small geometries, although it may be configured to be used on a variety of sizes of expandable spinal implants.

Expandable spinal implants of the present disclosure may be provided in multiple different sizes so as to accommodate the differing needs of a particular patient and operation. In some embodiments, the expandable spinal implant may be between 15 and 30 mm wide (e.g., the dimension between the first ends and second ends of the implants). In some embodiments, the expandable spinal implant may be between 18 and 26 mm wide. In some embodiments, the expandable spinal implant may be between 20 or 23 mm wide. In some embodiments, the expandable spinal implant may be between 40 and 60 mm long (i.e., the dimension between the lateral sides of the implants). In some embodiments, the expandable spinal implant may be between 40, 45, 50, 55, or 60 mm long.

Spinal implant systems of the present disclosure can be employed with a surgical arthrodesis procedure, such as, for example, an interbody fusion for treatment of an applicable condition or injury of an affected section of a spinal column and adjacent areas within a body, such as, for example, intervertebral disc space between adjacent vertebrae. In some embodiments, spinal implant systems can include an intervertebral implant that can be inserted with intervertebral disc space to space apart articular joint surfaces, provide support and maximize stabilization of the vertebrae. In some embodiments, spinal implant systems may be employed with one or a plurality of vertebra.

A medical practitioner obtains access to a surgical site including vertebrae such as through incision and retraction of tissues. Spinal implant systems of the present disclosure can be used in any existing surgical method or technique including open surgery, mini-open surgery, minimally invasive surgery and percutaneous surgical implantation, whereby vertebrae are accessed through a mini-incision, retractor, tube or sleeve that provides a protected passageway to the area, including, for example, an expandable retractor wherein the sleeve is formed from multiple portions that may be moved apart or together and may be inserted with the portions closed or together and then expanded to allow for insertion of implants of larger size than the closed cross section of the unexpanded retractor portions. In one embodiment, the components of the spinal implant system are delivered through a surgical pathway to the surgical site along a surgical approach into intervertebral disc space between vertebrae. Various surgical approaches and pathways may be used. Unilateral approaches such as a transforaminal lumbar interbody fusion (TLIF) approach may also be used to place the implant in a substantially oblique position relative to the vertebrae. Multilateral approaches such as those disclosed in U.S. Pat. No. 9,730,684, incorporated herein by reference in its entirety, may also be used with spinal implant systems of the present disclosure.

As will be appreciated by one of skill in the art, a preparation instrument (not shown) may be employed to remove disc tissue, fluids, adjacent tissues and/or bone, and scrape and/or remove tissue from endplate surfaces of the vertebrae in preparation for the procedures utilizing a system of the present disclosure. In some embodiments, the size of implant 10, 20, 30, 40 is selected after trialing using trialing instruments (not shown) that may approximate the size and configuration of the implants 10, 20, 30, 40. In some embodiments, such trials may be fixed in size and/or be fitted with expansion mechanisms similar to the various implant 10, 20, 30, 40 embodiments described herein. In some embodiments, implant 10, 20, 30, 40 may be visualized by fluoroscopy and oriented before introduction into intervertebral disc space. Furthermore, an insertion instrument and implants 10, 20, 30, 40 may be fitted with fiducial markers to enable image guided surgical navigation to be used prior to and/or during a procedure.

Components of a spinal implant system of the present disclosure including implant 10, 20, 30, 40 can be delivered or implanted as a pre-assembled device or can be assembled in situ. Components of spinal implant system including implant 10, 20, 30, 40 may be expanded, contracted, completely or partially revised, removed or replaced in situ. In some embodiments, one or all of the components of spinal implant system 10, 20, 30, 40 can be delivered to the surgical site via mechanical manipulation and/or a free hand technique.

In some embodiments, the spinal implant system includes an agent, including but not limited to the bone growth promoting materials BG described herein, which may be disposed, packed, coated or layered within, on or about the components and/or surfaces of the spinal implant system. In some embodiments the bone growth promoting materials may be pre-packed in the interior of the implant, and/or may be packed during or after implantation of the implant via a tube, cannula, syringe or a combination of these or other access instruments and may be further tamped into the implant before, during or after implantation. In some embodiments, the agent may include bone growth promoting material to enhance fixation of implant 10, 20, 30, 40 with bony structures. In some embodiments, the agent may include one or a plurality of therapeutic agents and/or pharmacological agents for release, including sustained release, to treat, for example, pain, inflammation and degeneration.

In one embodiment, implants 10, 20, 30, 40 may include fastening elements, which may include locking structure, configured for fixation with vertebrae to secure joint surfaces and provide complementary stabilization and immobilization to a vertebral region. In some embodiments, locking structure may include fastening elements, such as, for example, rods, plates, clips, hooks, adhesives and/or flanges. In some embodiments, the components of the spinal implant system can be used with screws to enhance fixation. The components of the spinal implant system can be made of radiolucent materials such as polymers. Radiopaque markers may be included for identification under x-ray, fluoroscopy, CT or other imaging techniques. The insertion instrument alone or with the tube for insertion therethrough described above may be radiolucent and may optionally include markers added at the tip and/or along the length of one or both of insertion instrument and the tube to permit them to be seen on fluoroscopy/x-ray while advancing into the patient. If the implant 10, 20, 30, 40 includes radiolucent markers placed near the second end this may permit visualization of the proximity of the tip of the tube moving toward the second end of the implant 10, 20, 30, 40.

In some embodiments, the use of microsurgical, minimally-invasive and image guided technologies may be employed to access, view and repair spinal deterioration or damage, with the aid of spinal implant system. Upon completion of the procedure, the non-implanted components, surgical instruments and assemblies of spinal implant system may be removed and the incision is closed. In some embodiments, the various instruments disclosed may be provided with fiducial markers or other elements suitable for use with surgical navigation systems (including, but not limited to the STEALTHSTATION® Navigation system available from Medtronic), such that a surgeon may view a projected trajectory or insertion pathway of the implants 10, 20, 30, 40 relative to a patient's anatomy in real time and/or in near-real time.

It will be understood that the various independent components of the expandable spinal implants 10, 20, 30, 40 described herein may be combined in different ways according to various embodiments. In particular, common numbering schemes in FIGS. 1-34 (e.g., 1xx, 2xx, 3xx, 4xx) indicate similar components of implants 10, 20, 30, 40.

It will be understood that various modifications may be made to the embodiments disclosed herein. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. An expandable spinal implant, the expandable spinal implant comprising:
  a first endplate, the first endplate including:
    a first outer surface and a first inner surface opposite the first outer surface, the first inner surface including a first plurality of ramps and at least one first channel;
    a first endplate first end and a first endplate second end opposite the first endplate first end, a first endplate first lateral surface and a first endplate second lateral surface opposite the first endplate first lateral surface;
  a second endplate, the second endplate including:
    a second outer surface and a second inner surface opposite the second outer surface, the second inner surface including a second plurality of ramps and at least one second channel;
    a second endplate first end and a second endplate second end opposite the second endplate first end, a second endplate first lateral surface and a second endplate second lateral surface opposite the second endplate first lateral surface,
  an expansion mechanism disposed between the first endplate and the second endplate, the expansion mechanism including:
    a first wedge disposed between the first endplate and second endplate, the first wedge including:
      a first wedge first end including a first upper surface and a first lower surface, a first wedge second end including a second upper surface and a second lower surface, wherein the first wedge comprises a first wedge aperture between the first wedge first end and the first wedge second end; and
      at least one first protrusion, each first protrusion being mated with a corresponding first channel of the at least one first channel;
    a second wedge disposed between the first endplate and second endplate, the second wedge including:
      a second wedge first end including a third upper surface and a third lower surface, a second wedge second end including a fourth upper surface and a fourth lower surface, wherein the second wedge comprises a second wedge aperture between the second wedge first end and the second wedge second end; and
      at least one second protrusion, each second protrusion being mated with a corresponding second channel of the at least one first channel;
    a first pin configured to prevent the first wedge from translating to far towards the first ends of the first and second endplates, the first pin extends from the first inner surface to the second inner surface without extending beyond the first outer surface or the second outer surface;
    a second pin configured to prevent the second wedge from translating to far towards the second ends of the first and second endplates, the second pin extends from the first inner surface to the second inner surface without extending beyond the first outer surface or the second outer surface;
    a rod assembly extending longitudinally with respect to the first and second endplates, the rod assembly defining a rotation axis, the rod assembly being disposed within the first wedge aperture and second wedge aperture, the rod assembly being configured to:
      expand the implant by: moving the first wedge towards the first ends of the first and second endplates, by moving the second wedge towards the second ends of the first and second endplates, and by moving the first wedge and second wedge away from one another to thereby increase a height between the first and second endplates, contract the implant by: moving the first wedge away from the first ends of the first and second endplates, by moving the second wedge away from the second ends of the first and second endplates, and by moving the first wedge and second wedge towards one another to thereby decrease a height between the first and second endplates, wherein the first wedge and second wedge are operably engaged with the first and second endplate via the first and second plurality of ramps, wherein each first protrusion and each second protrusion extend laterally away from the rod assembly in a direction substantially perpendicular to the rotation axis, wherein a first height measured between the first endplate first end and the second endplate first end is greater than a second height measured between the first endplate second end and the second endplate second end, wherein a height along the first end of the first wedge between the first upper surface and the first lower surface is substantially equal to a height along the second end of the first wedge between the second upper surface and the second lower surface, wherein a height along the first end of the second wedge between the third upper surface and the third lower surface is substantially equal to a height along the second end of the second wedge between the fourth upper surface and the fourth lower surface, wherein the first pin is disposed in a first pin aperture disposed at an end of a ramp of the first plurality of ramps such that in a maximum expanded position the first wedge will directly contact the first pin and be prevented from translating to far towards the first ends of the first and second endplates, and wherein the second pin is disposed in a second pin aperture disposed at an end of a ramp of the second plurality of ramps such that in a maximum expanded position the first wedge will directly contact the first pin and be prevented from translating to far towards the second ends of the first and second endplates.

2. The expandable spinal implant of claim 1, wherein the rod assembly comprises a first threaded outer surface along a first portion and a second threaded outer surface along a second portion, and wherein the first wedge aperture comprises a threaded inner surface operably engaged with the first threaded outer surface of the rod and the second wedge aperture comprises a threaded inner surface operably engaged with the second threaded outer surface of the rod.

3. The expandable spinal implant of claim 2, wherein the first threaded outer surface and the second threaded outer surface are threaded in opposite directions.

4. The expandable spinal implant of claim 1, wherein:
the first wedge further comprises a first plurality of protrusions including the at least one first protrusion, each protrusion of the first plurality of protrusions extending laterally away from the rod assembly in a direction substantially perpendicular to the rotation axis, and
the second wedge further comprises a second plurality of protrusions including the at least one second protrusion, each protrusion of the second plurality of protrusions extending laterally away from the rod assembly in a direction substantially perpendicular to the rotation axis.

5. The expandable spinal implant of claim 4, wherein:
the first inner surface comprises a plurality of channels including the at least one first channel,
the second inner surface comprises a plurality of channels including the at least one second channel,
the first plurality of protrusions is mated with the first plurality of channels, and
the second plurality of protrusions is mated with the second plurality of channels.

6. The expandable spinal implant of claim 1, wherein:
each ramp of the first plurality of ramps is inclined away from a medial portion of the first endplate toward a respective end of the first endplate first end or first endplate second end; and
each ramp of the second plurality of ramps is inclined away from a medial portion of the second endplate toward a respective end of the second endplate first end or second endplate second end.

7. The expandable spinal implant of claim 1, wherein:
the first wedge further comprises a first lateral surface extending between the first wedge first end and the first wedge second end, and an opposing first wedge second lateral surface extending between the first wedge first end and the first wedge second end;
the second wedge further comprises a third lateral surface extending between the second wedge first end and the second wedge second end, and an opposing second wedge fourth lateral surface extending between the second wedge first end and the second wedge second end, and
wherein the first lateral surface of the first wedge faces the third lateral surface of the second wedge.

8. The expandable spinal implant of claim 7, wherein
the first upper surface and the first lower surface of the first wedge first end are inclined away from the first lateral surface towards the second lateral surface of the first wedge,
the second upper surface and the second lower surface of the first wedge second end are inclined away from the first lateral surface towards the second lateral surface of the first wedge,
the third upper surface and the third lower surface of the second wedge first end are inclined away from the third lateral surface towards the fourth lateral surface of the second wedge, and
the fourth upper surface and the fourth lower surface of the second wedge second end are inclined away from the third lateral surface towards the fourth lateral surface of the second wedge.

9. The expandable spinal implant of claim 8, further comprising a retaining rod extending through the first endplate and second endplate in a direction substantially perpendicular to the rotation axis, the retaining rod being configured to prevent lateral displacement of the first endplate relative to the second endplate.

10. The expandable spinal implant of claim 8, wherein:
the first upper surface and the first lower surface of the first wedge first end are inclined away from the first lateral surface towards the second lateral surface of the first wedge by substantially the same degree as measured with respect to the rod,
the second upper surface and the second lower surface of the first wedge first end are inclined away from the first lateral surface towards the second lateral surface of the first wedge by substantially the same degree as measured with respect to the rod,
the third upper surface and the third lower surface of the second wedge first end are inclined away from the third lateral surface towards the fourth lateral surface of the second wedge by substantially the same degree as measured with respect to the rod, and the fourth upper surface and the fourth lower surface of the second wedge second end are inclined away from the third lateral surface towards the fourth lateral surface of the second wedge by substantially the same degree as measured with respect to the rod.

11. The expandable spinal implant of claim 8, wherein:

the first wedge first end and first wedge second end are symmetric with respect to one another, and the second wedge first end and second wedge second end are symmetric with respect to one another.

12. The expandable spinal implant of claim 11, wherein, when expanding the implant, the expansion mechanism is configured to move the first endplate and second endplate away from each other at the same rate such that a lordotic angle of the implant remains constant while a height of the implant increases.

13. The expandable spinal implant of claim 1, wherein:

the first endplate first lateral surface comprises at least one aperture configured to operably engage with an insertion instrument, and at least one end of the rod assembly comprises a drive interface configured to operably engage with an instrument.

14. An expandable spinal implant system, comprising:
a surgical instrument; and
the expandable spinal implant according to claim 1,
wherein the first endplate first lateral surface comprises at least one aperture configured to operably engage with the surgical instrument, and
wherein at least one end of the rod assembly comprises a drive interface configured to operably engage with the surgical instrument.

15. A method of deploying an expandable spinal implant, comprising:
providing a surgical instrument;
providing the expandable spinal implant according to claim 1;
engaging an aperture of the expandable spinal implant with the surgical instrument and positioning the expandable spinal implant within a vertebral space of a patient; and
engaging a drive interface of the expandable spinal implant and expanding the expandable spinal implant within the vertebral space of the patient.

16. The expandable spinal implant of claim 1, wherein the expansion mechanism is configured to maintain a lordotic angle defined by the first outer surface and the second outer surface.

17. The expandable spinal implant of claim 1, wherein:
the first pin extends from the first inner surface to the second inner surface without extending beyond the first outer surface or the second outer surface, and
the second pin extends from the first inner surface to the second inner surface without extending beyond the first outer surface or the second outer surface.

* * * * *